US010111901B2

(12) United States Patent
Bose et al.

(10) Patent No.: US 10,111,901 B2
(45) Date of Patent: *Oct. 30, 2018

(54) BETA-GLUCAN IN COMBINATION WITH ANTI-CANCER AGENTS AFFECTING THE TUMOR MICROENVIRONMENT

(71) Applicant: Biothera, Inc., Eagan, MN (US)

(72) Inventors: Nandita Bose, Plymouth, MN (US); Keith Gorden, Woodbury, MN (US); Anissa S H. Chan, Arden Hills, MN (US); Steven Leonardo, Rosemount, MN (US); Jeremy Graff, Indianapolis, IN (US); Xiaohong Qiu, Edina, MN (US); Takashi Kangas, Shoreview, MN (US); Kathryn A. Fraser, St. Paul, MN (US); Adria Bykowski Jonas, Eden Prairie, MN (US); Nadine Ottoson, Lakeville, MN (US); Ross Fulton, St. Paul, MN (US)

(73) Assignee: BIOTHERA, INC., Eagan, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/386,887

(22) Filed: Dec. 21, 2016

(65) Prior Publication Data
US 2017/0100425 A1 Apr. 13, 2017

Related U.S. Application Data

(63) Continuation of application No. PCT/US2015/039977, filed on Jul. 10, 2015.

(60) Provisional application No. 62/149,892, filed on Apr. 20, 2015, provisional application No. 62/115,895, filed on Feb. 13, 2015, provisional application No. 62/076,094, filed on Nov. 6, 2014, provisional application No. 62/022,754, filed on Jul. 10, 2014.

(51) Int. Cl.
A61K 31/716 (2006.01)
A61K 31/00 (2006.01)
A61K 39/39 (2006.01)
C07K 16/28 (2006.01)
C07K 16/30 (2006.01)
A61K 9/00 (2006.01)
C07K 16/44 (2006.01)
A61K 39/395 (2006.01)
A61K 39/00 (2006.01)

(52) U.S. Cl.
CPC .......... A61K 31/716 (2013.01); A61K 9/0019 (2013.01); A61K 39/3955 (2013.01); C07K 16/2827 (2013.01); C07K 16/303 (2013.01); C07K 16/3015 (2013.01); C07K 16/3023 (2013.01); C07K 16/3038 (2013.01); C07K 16/3046 (2013.01); C07K 16/3053 (2013.01); C07K 16/3061 (2013.01); C07K 16/44 (2013.01); A61K 2039/505 (2013.01)

(58) Field of Classification Search
None
See application file for complete search history.

(56) References Cited

U.S. PATENT DOCUMENTS

| 4,810,646 A | 3/1989 | Jamas et al. |
|---|---|---|
| 4,962,094 A | 10/1990 | Jamas et al. |
| 5,028,703 A | 7/1991 | Jamas et al. |
| 5,032,401 A | 7/1991 | Jamas et al. |
| 5,082,936 A | 1/1992 | Jamas et al. |
| 5,214,337 A | 5/1993 | Ishibashi |
| 5,250,436 A | 10/1993 | Jamas et al. |
| 5,322,841 A | 6/1994 | Jamas et al. |
| 5,397,773 A | 3/1995 | Donzis |
| 5,488,040 A | 1/1996 | Jamas et al. |
| 5,504,079 A | 4/1996 | Jamas et al. |
| 5,506,124 A | 4/1996 | Jamas et al. |
| 5,519,009 A | 5/1996 | Donzis |
| 5,532,223 A | 7/1996 | Jamas et al. |
| 5,576,015 A | 11/1996 | Donzis |
| 5,607,677 A | 3/1997 | Jamas et al. |
| 5,622,939 A | 4/1997 | Jamas et al. |
| 5,622,940 A | 4/1997 | Ostroff |
| 5,633,369 A | 5/1997 | Jamas et al. |
| 5,663,324 A | 9/1997 | James et al. |
| 5,702,719 A | 12/1997 | Donzis |
| 5,705,184 A | 1/1998 | Donzis |
| 5,741,495 A | 4/1998 | Jamas et al. |
| 5,783,569 A | 7/1998 | Jamas et al. |
| 5,811,542 A | 9/1998 | Jamas et al. |

(Continued)

FOREIGN PATENT DOCUMENTS

| CN | 101553261 A | 10/2009 |
|---|---|---|
| EP | 2032180 A2 | 3/2009 |

(Continued)

OTHER PUBLICATIONS

Chan et al. ("Chan", Journal of Hematoogy and Onclology, 2009, 2, 1-11).*

(Continued)

Primary Examiner — Misook Yu
Assistant Examiner — Kauser M Akhoon
(74) Attorney, Agent, or Firm — Wilson Sonsini Goodrich & Rosati

(57) ABSTRACT

The present invention relates to the combination of soluble β-glucan and anti-cancer agents that affect the tumor microenvironment. Soluble β-glucan promotes an immunostimulatory environment, which allows enhanced effectiveness of anti-cancer agents.

19 Claims, 36 Drawing Sheets

(56) References Cited

U.S. PATENT DOCUMENTS

| | | | |
|---|---|---|---|
| 5,817,643 | A | 10/1998 | Jamas et al. |
| 5,849,720 | A | 12/1998 | Jamas et al. |
| 6,020,324 | A | 2/2000 | Jamas et al. |
| 6,046,323 | A | 4/2000 | Park |
| 6,084,092 | A | 7/2000 | Wakshull et al. |
| 6,090,938 | A | 7/2000 | Wakshull et al. |
| 6,110,692 | A | 8/2000 | Wakshull et al. |
| 6,117,850 | A | 9/2000 | Patchen et al. |
| 6,143,731 | A | 11/2000 | Jamas et al. |
| 6,143,883 | A | 11/2000 | Lehmann et al. |
| 6,242,594 | B1 | 6/2001 | Kelly |
| 6,294,321 | B1 | 9/2001 | Wakshull et al. |
| 6,369,216 | B1 | 4/2002 | Patchen et al. |
| 6,413,715 | B2 | 7/2002 | Wakshull et al. |
| 6,630,310 | B1 | 10/2003 | Wakshull et al. |
| 7,022,685 | B2 | 4/2006 | Patchen et al. |
| 7,981,447 | B2 | 7/2011 | Cox |
| 2002/0032170 | A1 | 3/2002 | Jamas et al. |
| 2004/0014715 | A1 | 1/2004 | Ostroff |
| 2004/0082539 | A1 | 4/2004 | Kelly |
| 2004/0116380 | A1 | 6/2004 | Jamas et al. |
| 2005/0245480 | A1 | 11/2005 | Ostroff et al. |
| 2006/0009419 | A1 | 1/2006 | Ross et al. |
| 2006/0165700 | A1 | 7/2006 | Ostroff et al. |
| 2006/0247205 | A1 | 11/2006 | Patchen et al. |
| 2007/0042930 | A1 | 2/2007 | Ross et al. |
| 2007/0059310 | A1 | 3/2007 | Karel |
| 2008/0063650 | A1 | 3/2008 | Yan |
| 2008/0103112 | A1 | 5/2008 | Magee et al. |
| 2008/0108114 | A1 | 5/2008 | Cox et al. |
| 2008/0167268 | A1 | 7/2008 | Yan |
| 2009/0047288 | A1 | 2/2009 | Yan |
| 2009/0074761 | A1 | 3/2009 | Yan |
| 2009/0169557 | A1 | 7/2009 | Ross et al. |
| 2017/0304352 | A1 | 10/2017 | Magee et al. |

FOREIGN PATENT DOCUMENTS

| | | | |
|---|---|---|---|
| HK | 1138215 A1 | 10/2014 | |
| JP | H05503952 A | 6/1993 | |
| JP | H06107702 A | 4/1994 | |
| JP | 2001342257 A | 12/2001 | |
| JP | 2002105101 A | 4/2002 | |
| JP | 2006507239 A | 3/2006 | |
| JP | 2008500623 A | 1/2008 | |
| JP | 2009515512 A | 4/2009 | |
| JP | 2009540106 A | 11/2009 | |
| JP | 2011501691 A | 1/2011 | |
| JP | 2014025079 A | 2/2014 | |
| SG | 164426 | 9/2010 | |
| WO | WO-9103495 A1 | 3/1991 | |
| WO | WO-9404163 A1 | 3/1994 | |
| WO | WO-2004014320 A2 | 2/2004 | |
| WO | WO-2004033502 A1 | 4/2004 | |
| WO | WO-2005120251 A1 | 12/2005 | |
| WO | WO-2006121168 A1 | 11/2006 | |
| WO | WO-2007146416 A2 | 12/2007 | |
| WO | WO 2009014708 A2 * | 1/2009 | ........... A61K 38/193 |
| WO | WO-2012154680 A2 | 11/2012 | |
| WO | WO-2012167061 A1 | 12/2012 | |
| WO | WO-2012177624 A3 | 4/2013 | |
| WO | WO 2013079174 A1 * | 6/2013 | ......... A61K 39/3955 |
| WO | WO 2013165591 A1 * | 11/2013 | ........... A61K 31/716 |
| WO | WO-2016007876 A1 | 1/2016 | |
| WO | WO-2016073763 A2 | 5/2016 | |

OTHER PUBLICATIONS

Topalian et al. ("Topalian", New Eng. J. Med., 2012, 366, 2443-2454).*
Barbee et al. ("Barbee", Annals of Pharmacotherapy, 2015, 49, 907-937).*
Bendell et al. ("Bendell", J. Clin Oncology, 2014, http://ascopubs.org/doi/abs/10.1200/jco.2014.32.15_suppl.tps3114).*
Hamid et al. ("Hamid", N. Engl. J. Med., 2013, 369, 134-144).*
Gerson et al, WO 03/070234, p. 2, lines 7-15.*
Berenbaum (Clin. Exp Immunol. 28:1-18, 1977.*
Chou, T-C (Cancer Res. Jan. 15, 2010 70(2): 440-446).*
Wiesenthal (http://weisenthal.org/feedback. html, Feb. 4, 2002).*
Bacon et al. The glucan components of the cell wall of baker's yeast (Saccharomyces cerevisiae) considered in relation to its ultrastructure. Biochem J 114(3):557-567 (1969).
Bell et al. The structure of a cell-wall polysaccharide of Baker's yeast. J Chem Soc, pp. 1944-1947 (1950).
Blagovic et al. Lipid composition of brewer's yeast. Food Technol. Biotechnol. 39:175-181 (2001).
Daou et al. Oat Beta-Glucan: Its Role in Health Promotion and Prevention of Diseases. Comprehensive Reviews in Food Science and Food Safety 11:355-365 (2012).
Deman. Chapter 2. Lipids in Principles of Food Chemistry © 1985. AVI Publishing Co., Inc. (57 pgs.).
Hassid et al. The Molecular Constitution of an Insoluble Polysaccharide from Yeast, Saccharomyces cerevisiae. Contribution from the Divisions of Plant Nutrition and Fruit Products. College of Agriculture, University of California. pp. 295-298 (1941).
Hunter et al. Preparation of microparticulate beta-glucan from Saccharomyces cerevisiae for use in immune potentiation. Lett Appl Microbiol 35(4):267-271 (2002).
Manners et al. The structure of a β-(1→6)-d-glucan from yeast cell walls. Biochemical Journal 135:19-30 (1973).
Misaki et al. Structure of the cell-wall glucan of yeast (Saccharomyces cerevisiae). Carbohydrate Research 6(2):150-164 (1968).
Nawar. Chapter 4. Lipids in Food Chemistry. © 1985. Editor: Owen R. Fennema. Marcel Dekker, Inc. (110 pgs).
PCT/US2007/014055 International Preliminary Report on Patentability dated Dec. 16, 2008.
PCT/US2007/014055 International Search Report and Written Opinion dated Nov. 30, 2007.
PCT/US2015/039977 International Search Report and Written Opinion dated Oct. 13, 2015.
U.S. Appl. No. 60/975,734, filed Sep. 27, 2007.
U.S. Appl. No. 11/818,741 Office Action dated Aug. 9, 2013.
U.S. Appl. No. 11/818,741 Office Action dated Dec. 11, 2008.
U.S. Appl. No. 11/818,741 Office Action dated Dec. 29, 2015.
U.S. Appl. No. 11/818,741 Office Action dated Feb. 18, 2010.
U.S. Appl. No. 11/818,741 Office Action dated Feb. 7, 2014.
U.S. Appl. No. 11/818,741 Office Action dated Jul. 23, 2009.
U.S. Appl. No. 11/818,741 Office Action dated May 13, 2015.
U.S. Appl. No. 11/818,741 Office Action dated Nov. 4, 2014.
U.S. Appl. No. 11/818,741 Office Action dated Sep. 7, 2016.
Van Der Rest et al. The plasma membrane of Saccharomyces cerevisiae: structure, function, and biogenesis. Microbiol Rev. 59(2):304-322 (1995).
U.S. Appl. No. 15/386,781 Office Action dated Aug. 25, 2017.
Modak et al. Rituximab therapy of lymphoma is enhanced by orally administered (1→3),(1→4)-D-beta-glucan. Leuk Res 29(6):679-683 (2005).
Vasilakos. Abstract 5627: Antitumor 1-15 activity of soluble beta-1,3/1,6 glucans: Structure matters 1. Retrieved from the Internet: http://cancerres.aacrjournals.org/content/70/8Supplement/5627 on Dec. 4, 2017. Cancer Research (3 pgs.) (2010).

* cited by examiner

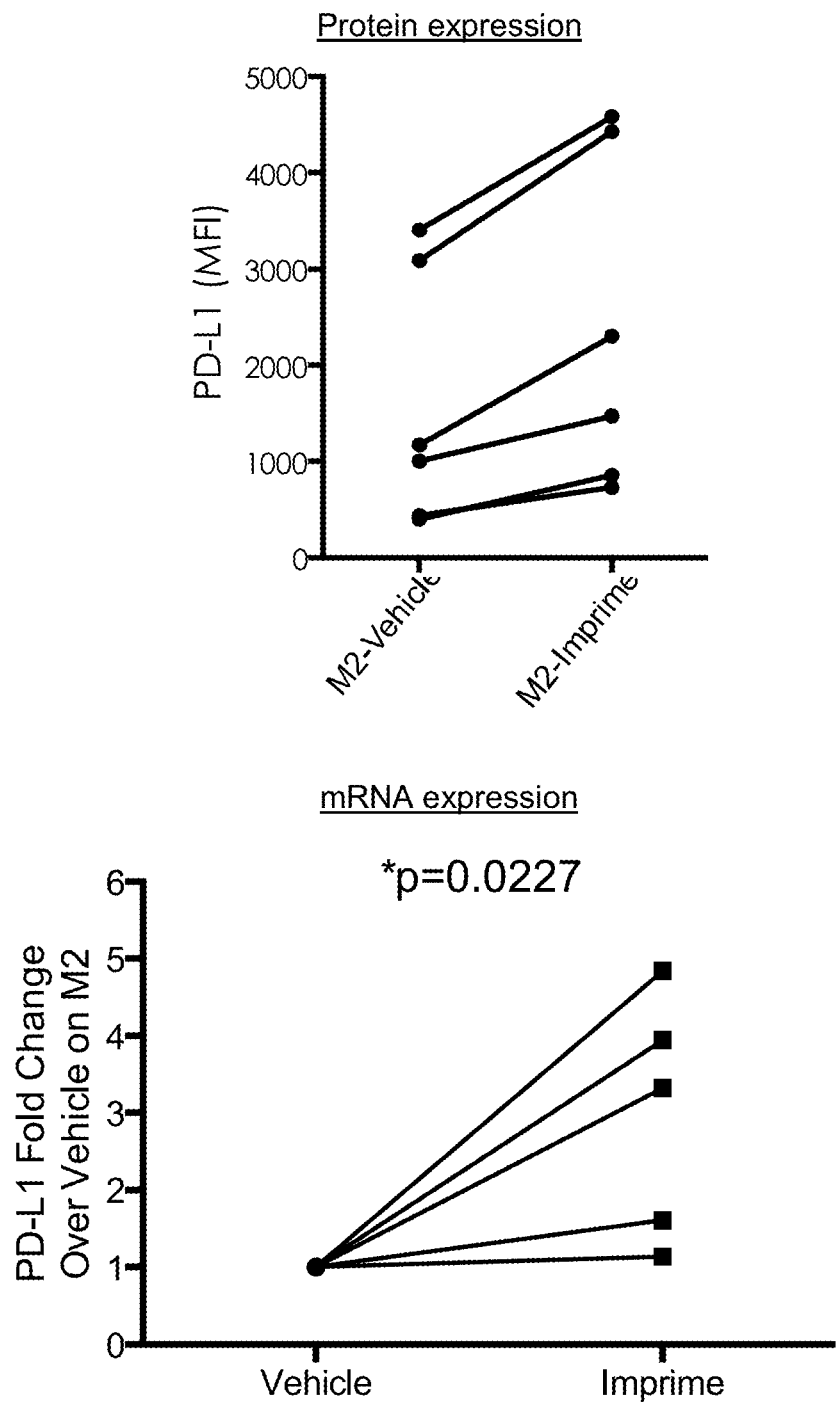

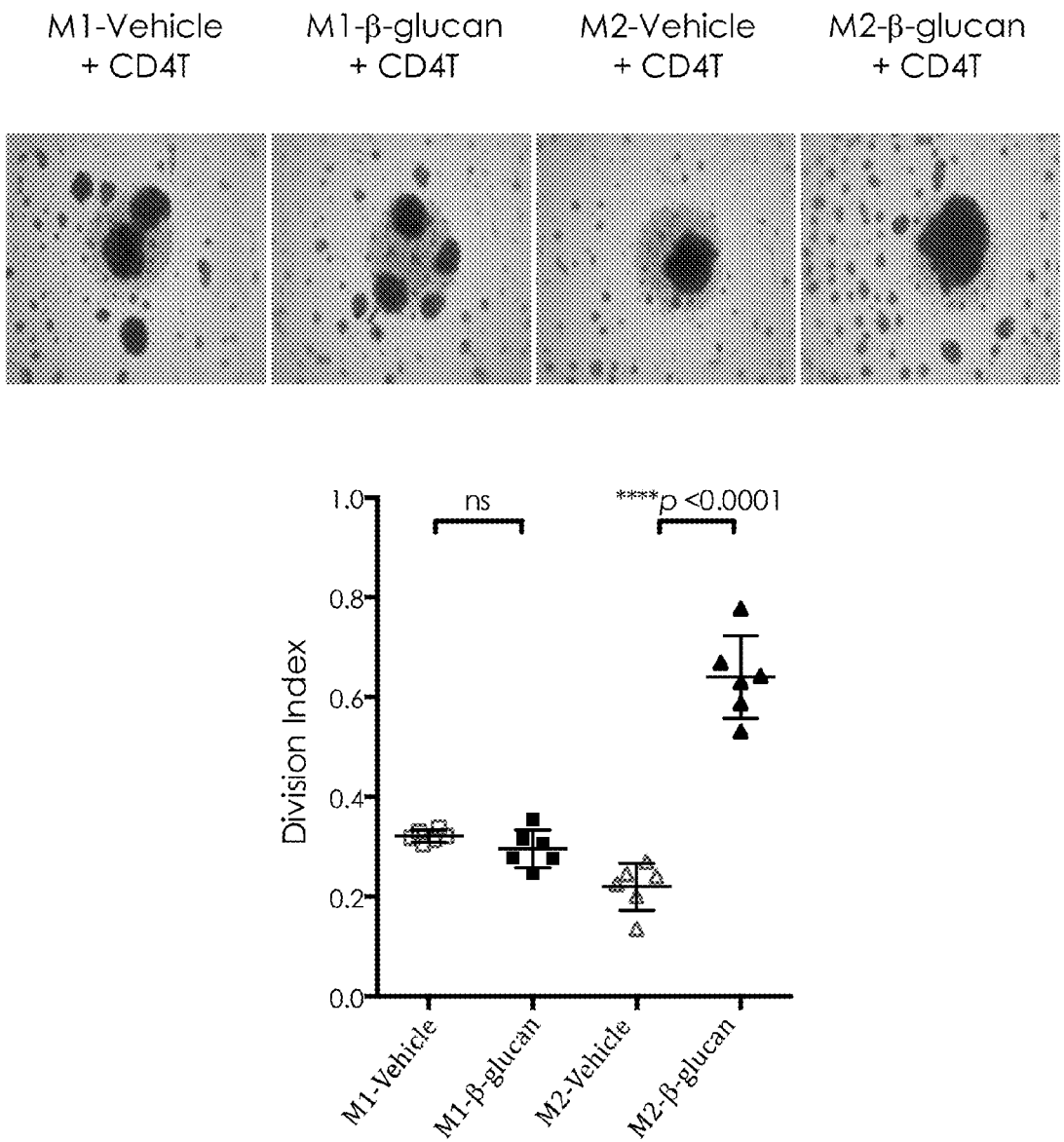

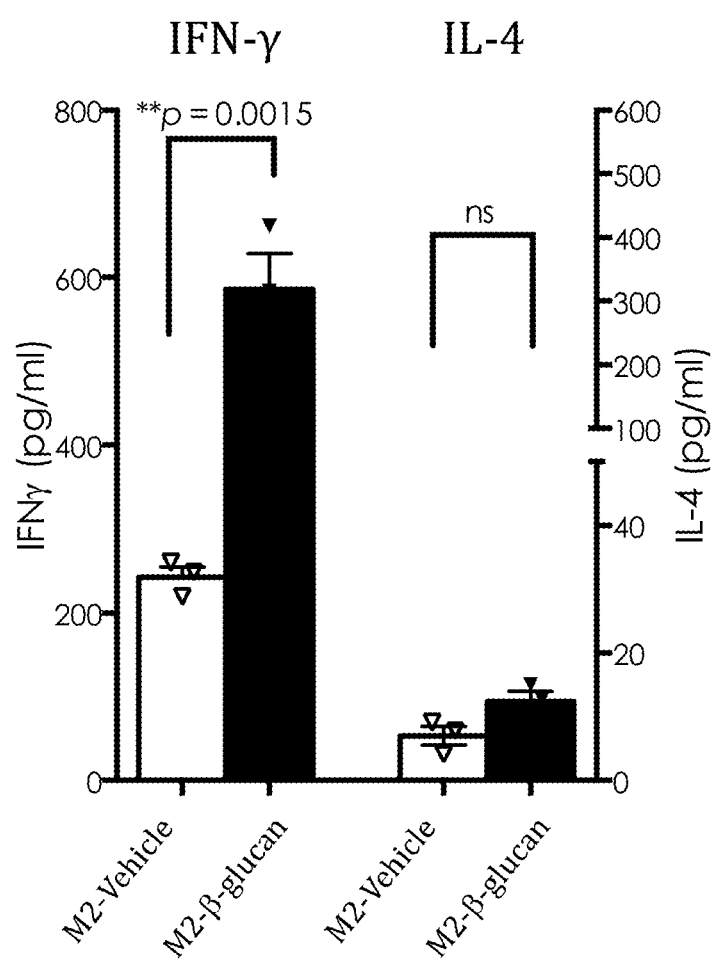

dendrites are indicated by the ➔ in the picture

High Binder

Low Binder

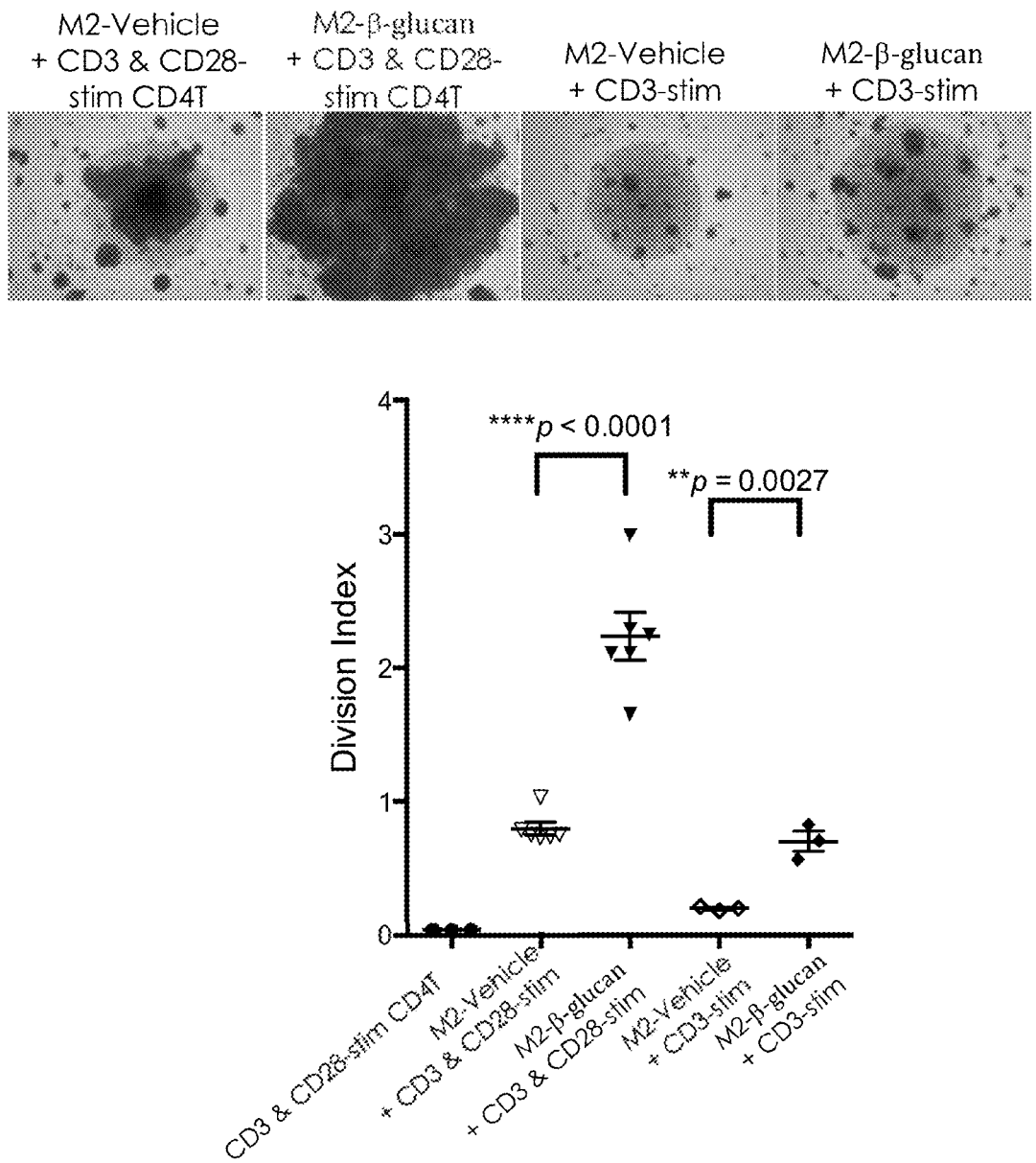

HB ABA (IgG): 1186 RAU/ml
LB ABA (IgG): 84 RAU/ml
Serum ABA is reported as RAU/ml (relative antibody units/ml)

p=0.0333 p=0.0239

BETA-GLUCAN IN COMBINATION WITH ANTI-CANCER AGENTS AFFECTING THE TUMOR MICROENVIRONMENT

CROSS-REFERENCE TO RELATED APPLICATION

This application is a continuation of International Application No. PCT/US2015/039977, filed Jul. 10, 2015; which claims priority to U.S. Provisional Patent Application Ser. Nos. 62/022,754 filed Jul. 10, 2014; 62/076,094 filed Nov. 6, 2014; 62/115,895 filed Feb. 13, 2015 and 62/149,892 filed Apr. 20, 2015, all of which are incorporated herein by reference in their entireties.

BACKGROUND OF THE INVENTION

The present invention relates to combinations of soluble β-glucan and anti-cancer agents that affect the tumor microenvironment, including immunosuppression-relieving anti-cancer agents. β-glucan is a fungal PAMP and is recognized by pattern recognition molecule C3 in the serum as well as pattern recognition receptor, complement receptor 3 (CR3) on the innate immune cells, including neutrophils and monocytes. β-glucan (β(1,6)-[poly-1,3)-D-glucopyranosyl]-poly-β(1,3)-D-glucopyranose), a polysaccharide β-glucan derived from yeast, is being developed as an immunotherapeutic agent in combination with anti-tumor monoclonal antibodies for the treatment of several cancers. β-glucan enables innate immune effector cells to kill complement-coated tumor cells through a complement CR3-dependent mechanism. Numerous animal tumor models have demonstrated that administration of soluble β-glucan in combination with a complement-activating, tumor-targeting antibody results in significantly reduced tumor growth and improved overall survival compared to either agent alone.

Cancers, however, are not just masses of malignant cells but complex "organs," which recruit and use many other non-transformed cells. Interactions between malignant and non-transformed cells create the tumor microenvironment (TME). The non-malignant cells of the TME have a dynamic and often tumor-promoting function at various stages of carcinogenesis. A complex and dynamic network of cytokines, chemokines, growth factors, and inflammatory and matrix-remodeling enzymes drive intercellular communication within the afflicted tissue. To effectively beat cancer, therefore, therapies must be developed to suppress the tumor-promoting nature of the TME.

SUMMARY OF THE INVENTION

This disclosure describes, in one aspect, uses and compositions of soluble β-glucan in combination with anti-cancer agents that affect the tumor microenvironment.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE FIGURES

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A-2D. Morphological, phenotypic and functional characterization of soluble β-glucan-treated M2 macrophages.

FIG. 3A-3D. Evaluations of CD4 T cell proliferation and modulation of IFN-γ and IL-4 production in β-glucan-treated M1 and M2 macrophages from high binders and low binders.

FIG. 8A-8C. Results of increased CD4 T cell proliferation by M2-β-glucan due to cell-to-cell contact.

DETAILED DESCRIPTION OF ILLUSTRATIVE EMBODIMENTS

Figure 1A:
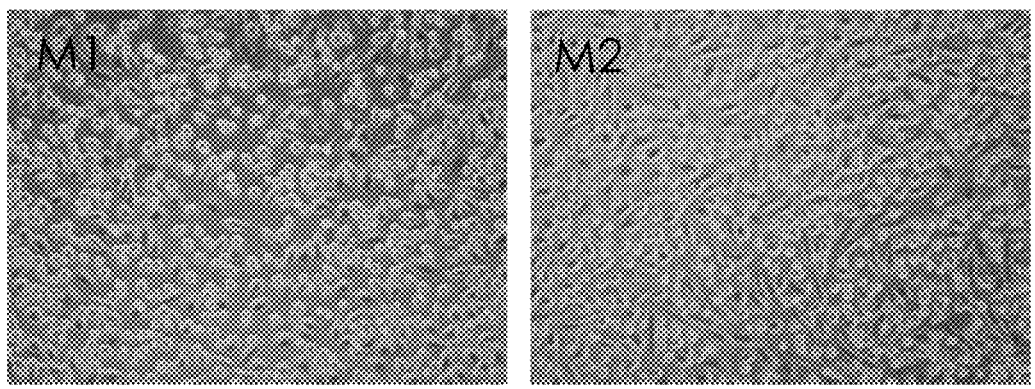
FIG. 1A-1D. Morphologic and functional characterization of in vitro cultured human M1 and M2 macrophages.

β-glucans are polymers of glucose derived from a variety of microbiological and plant sources including, for example, yeast, bacteria, algae, seaweed, mushroom, oats, and barley. Of these, yeast β-glucans have been extensively evaluated for their immunomodulatory properties. Yeast β-glucans can be present as various forms such as, for example, intact yeast, zymosan, purified whole glucan particles, solubilized zymosan polysaccharide, or highly-purified soluble β-glucans of different molecular weights. Structurally, yeast β-glucans are composed of glucose monomers organized as a β-(1,3)-linked glucopyranose backbone with periodic β-(1,3) glucopyranose branches linked to the backbone via β-(1,6) glycosidic linkages. The different forms of yeast β-glucans can function differently from one another. The mechanism through which yeast β-glucans exert their immunomodulatory effects can be influenced by the structural differences between different forms of the β-glucans such as, for example, its particulate or soluble nature, tertiary conformation, length of the main chain, length of the side chain, and frequency of the side chains. The immune stimulating functions of yeast β-glucans are also dependent upon the receptors engaged in different cell types in different species, which again, can be dependent on the structural properties of the β-glucans.

In general, β-glucan immunotherapies can include administering to a subject any suitable form of β-glucan or any combination of two or more forms of β-glucan. Suitable β-glucans and the preparation of suitable β-glucans from their natural sources are described in, for example, U.S. Patent Application Publication No. US2008/0103112 A1. In some cases, the β-glucan may be derived from a yeast such as, for example, Saccharomyces cerevisiae. In certain cases, the β-glucan may be or be derived from β(1,6)-[poly-(1,3)-D-glucopyranosyl]-poly-β(1,3)-D-glucopyranose, also referred to herein as PGG (IMPRIME PGG, Biothera, Eagan, Minn.), a highly purified and well characterized form of soluble yeast-derived β-glucan. Moreover, β-glucan-based immunotherapies can involve the use of, for example, a modified and/or derivatized β-glucan such as those described in International Patent Application No. PCT/US12/36795. In other cases, β-glucan immunotherapy can involve administering, for example, a particulate-soluble β-glucan or a particulate-soluble β-glucan preparation, each of which is described in, for example, U.S. Pat. No. 7,981,447.

Anticancer immunotherapeutic drugs kill cancer cells through multiple modalities: 1) direct activation of innate immune cells, 2) direct activation of adaptive immune cells, 3) indirect activation of both innate and adaptive immune cells by either making tumor cells more immunogenic or by subverting tumor-induced immunosuppression.

There is mounting evidence that myeloid cells at the tumor microenvironment (TME), including M2 macrophages, N2 neutrophils and myeloid-derived suppressor cells (MDSC), play a critical role in immune suppression by directly causing functional exhaustion of the cytotoxic T cells or by indirectly increasing the suppressive power of T-regulatory cells (Tregs). This leads to a skewed immunostimulatory versus immunosuppressive balance in the TME. The immunostimulatory environment of the TME is largely shaped by the presence of cytotoxic T cells and NK cells, cytolytic and phagocytosis-inducing M1 macrophages, cytotoxic N1 neutrophils, humoral response inducing B cells, and antigen presenting immunogenic dendritic cells (DC). Immunostimulatory cytokines and chemokines such as interferon gamma (IFN-γ), interleukin-12 (IL-12), tumor necrosis factor-alpha (TNF-α), etc. are key coordinators of the immunostimulatory activity. Important players that bias the immunosuppressive nature of the TME are anti-inflammatory Th2 cells, N2 neutrophils, M2 macrophages, Tregs, and tolerogenic DC. Immunosuppressive cytokines and chemokines such as transforming growth factor-beta (TGF-β), interleukin-10 (IL-10), macrophage colony stimulating factor (M-CSF), interleukin-4 (IL-4), etc. are key coordinators of the immunosuppressive activity.

Soluble β-glucan, by virtue of being a pathogen associated molecular pattern (PAMP) that binds to CD11b on cells of myeloid origin, namely neutrophils and monocytes, binds and increases the immunostimulatory functions of N1 neutrophils and M1 macrophages and decreases the immunosuppressive functions of MDSCs, N2 neutrophils and M2 macrophages. This modulation leads to cross-talk between the different innate and adaptive cell-subsets in the TME and eventually tilts the balance towards immunostimulation. More specifically, once bound to peripheral blood monocytes, soluble β-glucan modulates the differentiation of monocytes to macrophages in M1/anti-tumorigenic versus M2/pro-tumorigenic polarizing conditions such that M1 polarization is enhanced which increases macrophage immunostimulatory functions and M2 polarization is inhibited which decreases macrophage immunosuppressive functions. Soluble β-glucan directly affects M2 repolarization to the M1 phenotype and drives Th1 polarization, and soluble β-glucan-primed innate immune cells generate cytokines to indirectly affect CD4 and CD8 T cell proliferation, even in the presence of Tregs, and eventually drive Th1 polarization.

Soluble β-glucan elicits an adaptive immune response via the two innate cell subsets that are known to bridge innate and adaptive immune responses, monocyte-derived macrophages and dendritic cells and will upregulate PD-L1 expression on both monocyte-derived macrophages and dendritic cells. In spite of PD-L1 upregulation, soluble β-glucan-treated monocyte-derived macrophages and dendritic cells enhance T cell activation and proliferation, and the coordinated immune response elicited by soluble β-glucan elicits a tumor response akin to adaptive immune resistance, i.e., upregulation of surface expression of PD-L1.

Soluble β-glucan can be combined with non-complement activating, tumor-targeting immune suppression-relieving MAbs. For example, soluble β-glucan can be combined with anti-PD-L1 immune checkpoint inhibitors (Fc-engineered IgG1 MAb) in the treatment of several cancers, including, melanoma, renal cell carcinoma, lung cancer, etc. The efficacy of anti-PD1/PD-L1 antibodies has been reported to be dependent upon the expression level of PD-L1 on tumors. One of the mechanisms of PD-L1 expression on tumors is called adaptive immune resistance where PD-L1 expression is adaptively induced as a consequence of immune responses within the tumor microenvironment (e.g., interferon gamma production by activated T-cells). Soluble β-glucan either directly, or indirectly induces Th1 polarization. This effect upregulates the expression of PD-L1 on tumor cells, and thereby enhance the anti-tumor activity of anti-PD1/PD-L1 antibodies. Examples of checkpoint inhibitors are nivolumab and pembrolizumab.

Soluble β-glucan can be combined with non-complement activating, non-tumor targeting MAbs that enhance immune co-stimulation. For example, a) anti-CD40 MAb (IgG2 MAb), targeting dendritic cells, b) anti-OX40, anti-41BB, enhancer of T-cells co-stimulation in the treatment of several cancers.

Soluble β-glucan can also be combined with non-complement activating, non tumor-targeting immune suppression-relieving small molecules and non-complement activating, tumor-targeting immune suppression-relieving small molecules. It can be used as an adjuvant in cancer vaccines to drive Th1 polarization. It can be used therapeutically to decrease suppressive mechanisms in chronic diseases (i.e. TB) to hasten full clearance of the infection. Lastly, it can be use to skew the Th2-Th1 balance in Th2-dominant autoimmune diseases (allergies, asthma, atopic diseases) to a Th1-polarized environment.

Although non-complement activating immune suppression-relieving agents may be preferred, especially for non-tumor targeting agents, the invention may also be carried out with complement activating immune suppression-relieving agents. One example may be bavituximab.

The invention includes, in part, co-administering a β-glucan with another pharmaceutical agent, which, as used herein, may be an antibody preparation or a small molecule preparation or any preparation administered for affecting the TME. As used herein, "co-administered" refers to two or more components of a combination administered so that the therapeutic or prophylactic effects of the combination can be greater than the therapeutic or prophylactic effects of either component administered alone. Two components may be co-administered simultaneously or sequentially. Simultaneously co-administered components may be provided in one or more pharmaceutical compositions. Sequential co-administration of two or more components includes cases in which the components are administered so that both components are simultaneously bioavailable after both are administered. Regardless of whether the components are co-administered simultaneously or sequentially, the components may be co-administered at a single site or at different sites.

In another aspect, the method includes administering to a subject a composition that includes a β-glucan moiety conjugated to an antibody, a therapeutic antibody, an anti-tumor antibody or an antibody fragment such as the Fc portion of an antibody. Modified and/or derivatized soluble β-glucan, including β-glucan conjugates of a β-glucan moiety and an antibody are described in International Patent Application No. PCT/US12/36795, which may also be applied to conjugates of antibody fragments. The β-glucan moiety may be, or be derived from a β-1,3/1,6 glucan. In this context, "derived from" acknowledges that a conjugate may necessarily be prepared by creating a covalent linkage that replaces one or more atoms of the β-glucan. As used herein, "derived from a β-1,3/1,6 glucan" refers to a portion of the β-glucan that remains as part of a conjugate after replacing one or more atoms of the β-glucan to form the covalent linkage of the conjugate.

The β-glucan, the antibody or small molecule preparation, and/or the combination of both components may be formulated in a composition along with a "carrier." As used herein, "carrier" includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the β-glucan or the antibody, its use in the therapeutic compositions is contemplated. Supplementary active ingredients also can be incorporated into the compositions.

By "pharmaceutically acceptable" is meant a material that is not biologically or otherwise undesirable, i.e., the material may be administered to an individual along with the β-glucan and/or the pharmaceutical agent without causing any undesirable biological effects or interacting in a deleterious manner with any of the other components of the pharmaceutical composition in which it is contained.

The β-glucan, the pharmaceutical agent, and/or the combination of both components may be formulated into a pharmaceutical composition. In some embodiments, the β-glucan and the pharmaceutical agent may be provided in a single formulation. In other embodiments, the β-glucan and the pharmaceutical agent may be provided in separate formulations. A pharmaceutical composition may be formulated in a variety of and/or a plurality forms adapted to one or more preferred routes of administration. Thus, a pharmaceutical composition can be administered via one or more known routes including, for example, oral, parenteral (e.g., intradermal, transcutaneous, subcutaneous, intramuscular, intravenous, intraperitoneal, etc.), or topical (e.g., intranasal, intrapulmonary, intramammary, intravaginal, intrauterine, intradermal, transcutaneous, rectally, etc.). A pharmaceutical composition, or a portion thereof, can be administered to a mucosal surface, such as by administration to, for example, the nasal or respiratory mucosa (e.g., by spray or aerosol). A pharmaceutical composition, or a portion thereof, also can be administered via a sustained or delayed release.

A formulation may be conveniently presented in unit dosage form and may be prepared by methods well known in the art of pharmacy. Methods of preparing a composition with a pharmaceutically acceptable carrier include the step of bringing the β-glucan and/or the pharmaceutical agent into association with a carrier that constitutes one or more accessory ingredients. In general, a formulation may be prepared by uniformly and/or intimately bringing the active compound into association with a liquid carrier, a finely divided solid carrier, or both, and then, if necessary, shaping the product into the desired formulations.

The β-glucan, the pharmaceutical agent, and/or the combination of both components may be provided in any suitable form including but not limited to a solution, a suspension, an emulsion, a spray, an aerosol, or any form of mixture. The composition may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a lotion, and the like. The formulation may further include one or more additives including such as, for example, an adjuvant, a skin penetration enhancer, a colorant, a fragrance, a flavoring, a moisturizer, a thickener, and the like.

In some embodiments, the β-glucan may be derived from yeast such as, for example, Saccharomyces cerevisiae. In some embodiments, the β-glucan can include a β-1,3/1,6 glucan such as, for example, β(1,6)-[poly-(1,3)-D-glucopyranosyl]-poly-β(1,3)-D-glucopyranose.

In some embodiments, the method can include administering sufficient β-glucan to provide a dose of, for example, from about 100 ng/kg to about 50 mg/kg to the subject, although in some embodiments the methods may be performed by administering the β-glucan in a dose outside this range. In some embodiments, the method includes administering sufficient β-glucan to provide a dose of from about 10 µg/kg to about 5 mg/kg to the subject, for example, a dose of about 4 mg/kg.

Alternatively, the dose may be calculated using actual body weight obtained just prior to the beginning of a treatment course. For the dosages calculated in this way, body surface area ($m^2$) is calculated prior to the beginning of the treatment course using the Dubois method: $m^2 = (wt\ kg^{0.425} \times height\ cm^{0.725}) \times 0.007184$. In some embodiments, therefore, the method can include administering sufficient β-glucan to provide a dose of, for example, from about 0.01 $mg/m^2$ to about 10 $mg/m^2$.

In some embodiments, the method can include administering sufficient antibody that specifically binds the β-glucan to provide a dose of, for example, from about 100 ng/kg to about 50 mg/kg to the subject, although in some embodiments the methods may be performed by administering the antibody in a dose outside this range. In some embodiments, the method includes administering sufficient antibody to provide a dose of from about 10 μg/kg to about 5 mg/kg to the subject, for example, a dose of from about 100 μg/kg to about 1 mg/kg.

Alternatively, the dose may be calculated using actual body weight obtained just prior to the beginning of a treatment course. For the dosages calculated in this way, body surface area (m$^2$) is calculated prior to the beginning of the treatment course using the Dubois method: m$^2$=(wt kg$^{0.425}$×height cm$^{0.725}$)×0.007184. In some embodiments, therefore, the method can include administering sufficient antibody to provide a dose of, for example, from about 0.01 mg/m$^2$ to about 10 mg/m$^2$.

In some embodiments, the β-glucan and pharmaceutical agent may be co-administered, for example, from a single dose to multiple doses per week, although in some embodiments the method may be performed by co-administering the β-glucan and pharmaceutical agent at a frequency outside this range. In certain embodiments, the β-glucan and pharmaceutical agent may be administered from about once per year to once per week.

The term "and/or" means one or all of the listed elements or a combination of any two or more of the listed elements; the terms "comprises" and variations thereof do not have a limiting meaning where these terms appear in the description and claims; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Establishment and Characterization of In Vitro Cultured Human M1 and M2 Macrophages:

CD14$^+$ monocytes from human whole blood were enriched using Ficoll gradient and magnetic bead separation. Enriched monocytes (5×10$^5$ cells per mL) were then cultured in either M1-polarizing (XVivo 10 media (Lonza Group) supplemented with 5% autologous serum and 100 ng/mL recombinant human granulocyte macrophage colony-stimulating factor (rhGM-CSF) (R&D Systems) or M2-polarizing (XVivo 10 media supplemented with 10% autologous serum and 50 ng/mL recombinant human macrophage colony-stimulating factor (rhM-CSF) (R&D Systems) conditions for 6 days. In experiments performed to evaluate the effect of β-glucan, whole blood was first incubated with vehicle (sodium citrate buffer) or 25 μg/mL soluble β-glucan for 2 hours at 37° C. and then the monocytes were isolated and differentiated. Morphology was checked before macrophages were harvested for phenotypic analysis. Culture medium of the day 6 macrophage culture (MCM) was collected, spun down to remove contaminated cell pellet and then frozen down for subsequent cytokine analysis by ELISA or used to setup a co-culture with CD3 & CD28-stimulated CD4 T cells (MCM-CD4 T) for evaluation of either surface markers or CD4 T cell proliferation. The macrophages were used to setup a co-culture with CD3 & CD28- or CD3 only-stimulated CD4 T cells (Mac-CD4 T) on day 6 for evaluation of either surface marker modulation or effect on CD4 T cell proliferation. For Mac-CD4 T cell proliferation study, M1 or M2 macrophages were cultured with CD3 & CD28- or CD3 only-stimulated, CFSE-labeled, autologous CD4 T cells at a 1:10 ratio. T cell proliferation was measured at the end of the experiment (day 9-day 11) by flow cytometry, and results are graphically shown as CFSE-dilution peaks. The assessment of CD3-only stimulated T cells was always done on day 11. Quantitative results were reported as the Division Index (the average number of cell divisions a population underwent) calculated for each of the triplicate wells in each of the culture conditions. Culture supernatants of Mac-CD4 T co-cultures were collected for subsequent cytokine analysis.

For evaluation of Mac-CD4 T cell surface marker modulation, M2 macrophages were co-cultured with T cells as described above and cells were harvested on day 8, day 9 and day 10 to perform surface receptor staining on both M2 macrophages and T cells.

For MCM-CD4 T cell proliferation study, CD3 & CD28-stimulated, CFSE-labeled CD4 T cells were cultured with 50% MCM. T cell proliferation was measured on day 11 as described above. Culture supernatants of the MCM-CD4 T cell co-culture were collected for subsequent cytokine analysis. MCM-CD4 T cell surface marker evaluation was performed as described above.

Figure 1B:
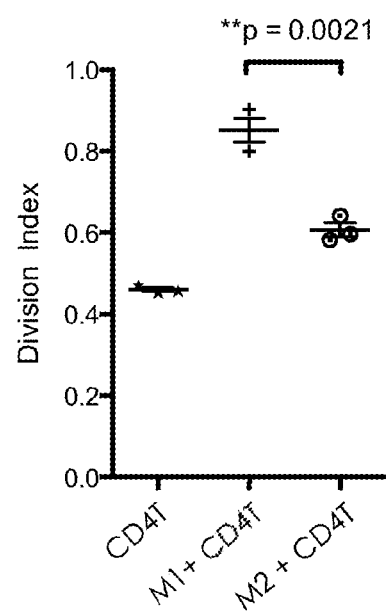
Figure 1C:
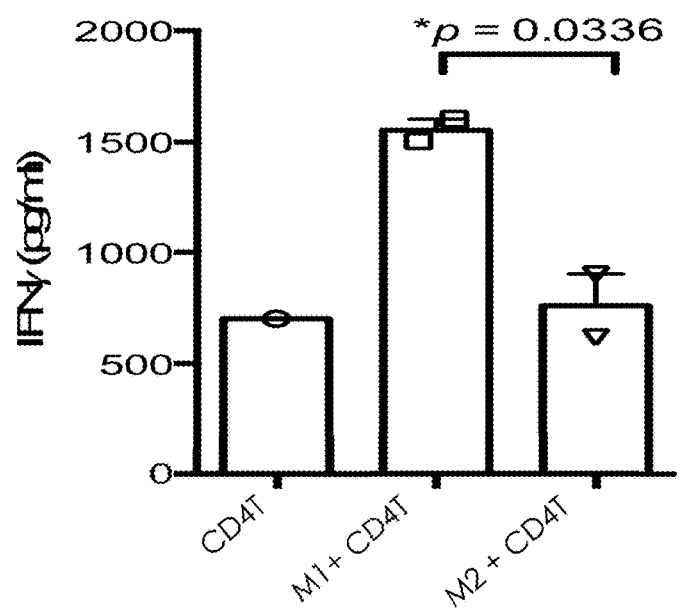

M1 and M2 macrophages were prepared and characterized as described above were characterized for A) morphology, B) phenotype, C) functional evaluation of Mac-CD4 T cell proliferation and D) cytokine analysis in the co-cultures. FIG. 1A-FIG. 1C include representative results from 5 different experiments.

As per literature, the morphology of M1 appeared more rounded and M2 were more elongated fibroblast-like (FIG. 1A). Expression of M1/M2-specific markers was evaluated by flow cytometry. Median MFI was calculated for isotype control staining and surface antigen staining and the results are shown in Table 1.

TABLE 1

| | | HLA-DR | CD163 | CD14 | CD206 | CD209 | CD80 | CD86 | CD274 (PD-L1) |
|---|---|---|---|---|---|---|---|---|---|
| M1 | Isotype control | 91 | 91 | 23 | 151 | 127 | 151 | 127 | 91 |
| | Surface antigen | 1715 | 148 | 100 | 859 | 1535 | 179 | 2218 | 3570 |
| M2 | Isotype control | 99 | 99 | 21 | 147 | 144 | 147 | 144 | 99 |
| | Surface antigen | 1054 | 1732 | 805 | 411 | 538 | 167 | 2463 | 385 |

Consistent with literature regarding phenotype, M1 macrophages typically expressed higher levels of HLA-DR and CD274 (PD-L1), while M2 macrophages expressed higher levels of CD163 and CD14. Additionally, in comparison to in vitro differentiated M2 macrophages, M1 macrophages also significantly helped CD4 T cells to proliferate as shown in FIG. 1B. Concomitant with enhanced proliferation, increased production of interferon gamma (IFN-γ) was observed in the supernatants of M1 and CD4 T cell co-cultures (FIG. 1C).

Steps for an alternative method for in vitro culture and characterization of human macrophages that includes activation of M1 and M2 macrophages (designated M1a and M2a macrophages) are outlined below. This methodology was used in the next series of experiments.

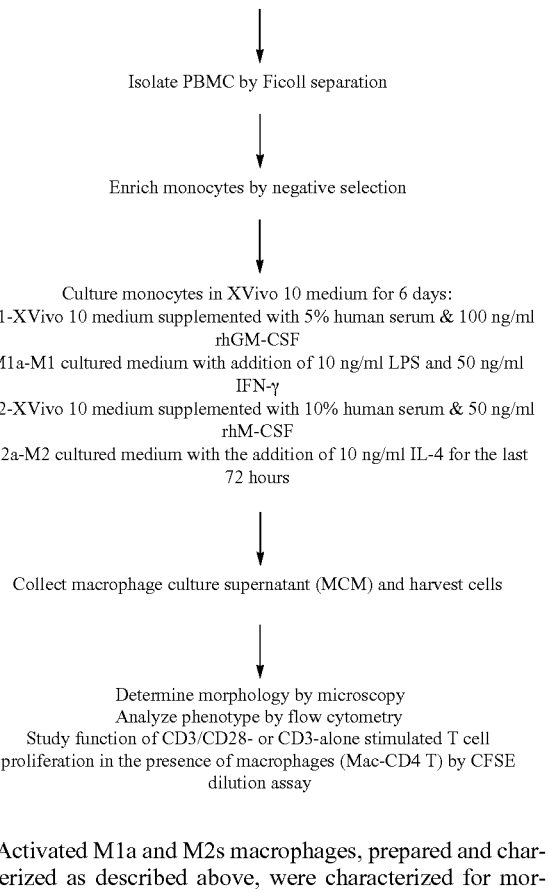

Activated M1a and M2s macrophages, prepared and characterized as described above, were characterized for morphology and phenotype. Shown here are representative results from 5 different experiments.

Figure 1D:
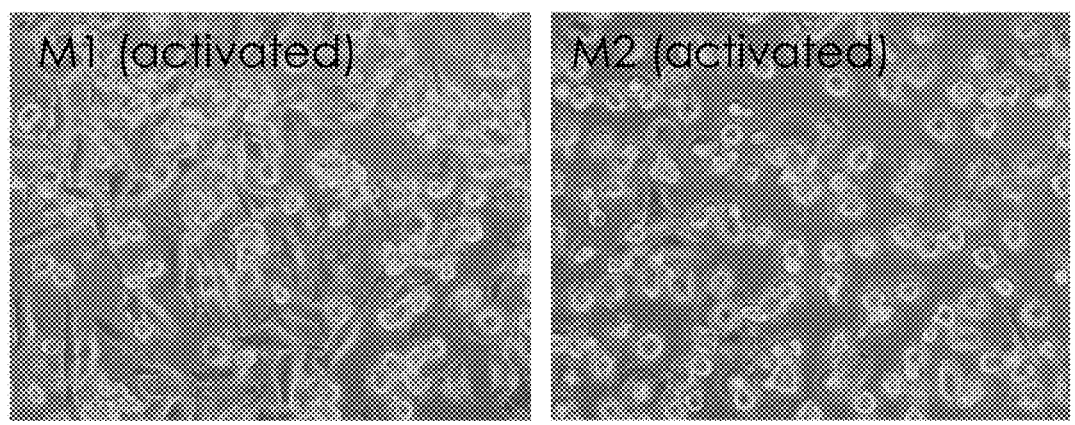

FIG. 1D shows the morphology of M1a and M2a macrophages. Expression of M1a/M2a-specific markers was evaluated by flow cytometry. Median MFI was calculated for isotype control staining and surface antigen staining and the results are shown in Table 2.

TABLE 2

|     |                  | HLA-DR | CD163 | CD14 | CD206 | CD209 | CD80 | CD86 | CD274 (PD-L1) |
|-----|------------------|--------|-------|------|-------|-------|------|------|---------------|
| M1a | Isotype control  | 123    | 123   | 23   | 119   | 79    | 119  | 79   | 23            |
|     | Surface antigen  | 1535   | 812   | 191  | 1005  | 1215  | 537  | 3187 | 26135         |
| M2a | Isotype control  | 85     | 85    | 25   | 112   | 97    | 112  | 97   | 85            |
|     | Surface antigen  | 1800   | 3509  | 614  | 2186  | 4482  | 230  | 2445 | 4471          |

Example 2

Figure 2A:
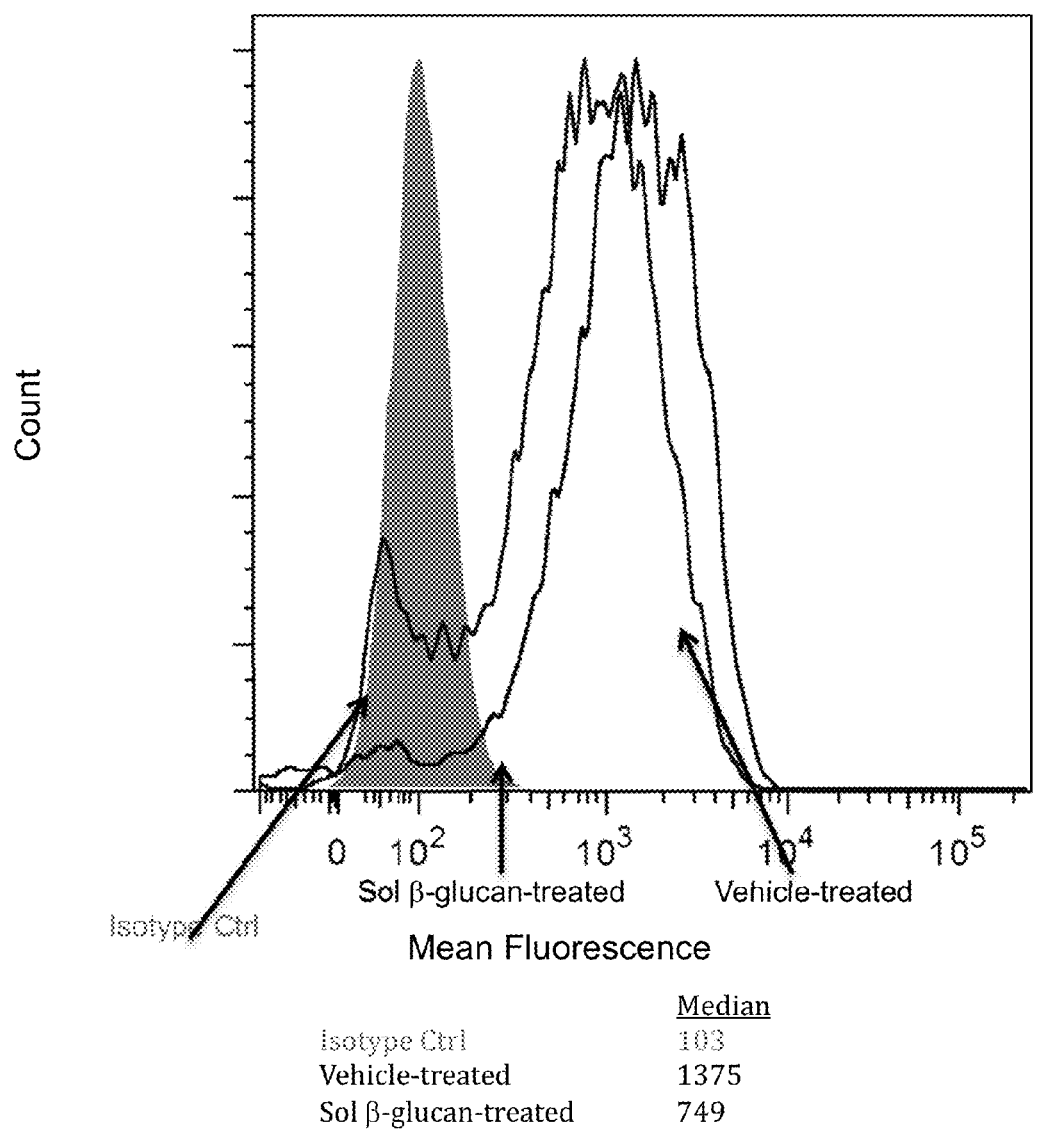

Effect of β-Glucan on M2 to M1 Repolarization:

M1 and M2 macrophages from vehicle- or β-glucan-treated whole blood were prepared as described above. An expression of a panel of M1/M2-specific markers (including HLA-DR, CD163, CD206, CD209, CD80, CD86 and PD-L1) were measured by flow cytometry. β-glucan pre-treatment did not affect M1 macrophage phenotype but did affect M2 macrophage phenotype. As shown in FIG. 2A, mean fluorescence intensity (MFI) of CD163 is downmodulated in β-glucan-treated M2 macrophages. In addition, surface expression of CD86 was enhanced as well as both protein and mRNA levels of PD-L1 (FIG. 2B).

Figure 2C:
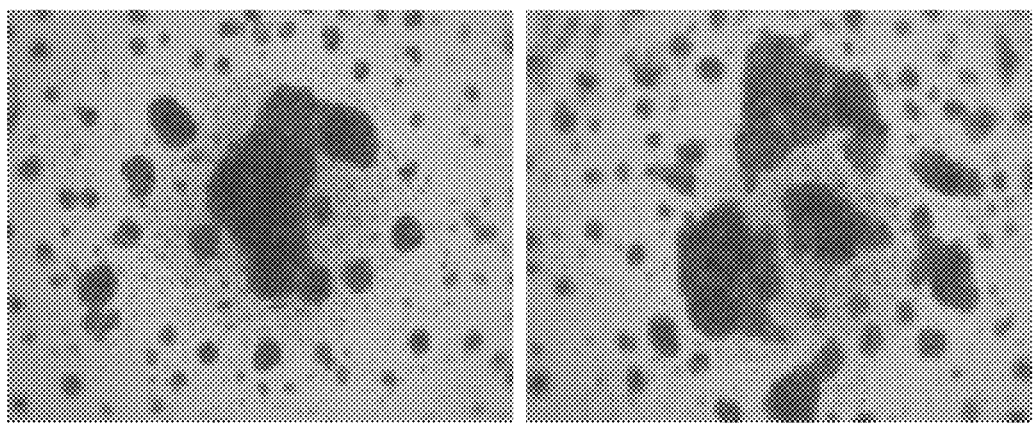
Figure 2C:
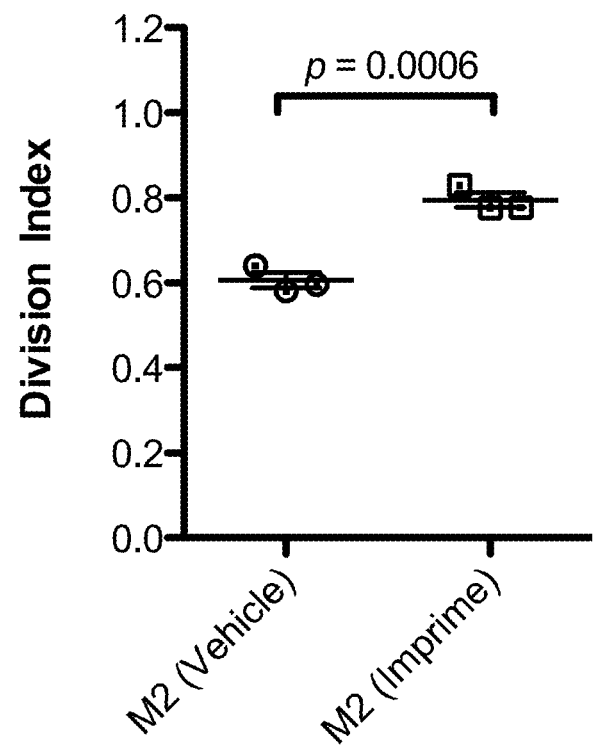

Next, vehicle- or β-glucan-treated M1 or M2 macrophages were cultured with CD3 and CD28-stimulated, carboxyfluorescein diacetate succinimidyl ester (CFSE)-labeled autologous CD4 T cells and T cell proliferation was measured at the end of the experiment by flow cytometry and results quantitatively reported as division index (the average number of cell divisions a population has undergone). FIG. 2C is a representative CFSE dilution T-cell proliferation assay performed by co-culturing T-cells with β-glucan-treated M2 macrophages, and the results show the ability of the β-glucan-treated M2 macrophages to enhance CD4 T cell proliferation.

Figure 2D:
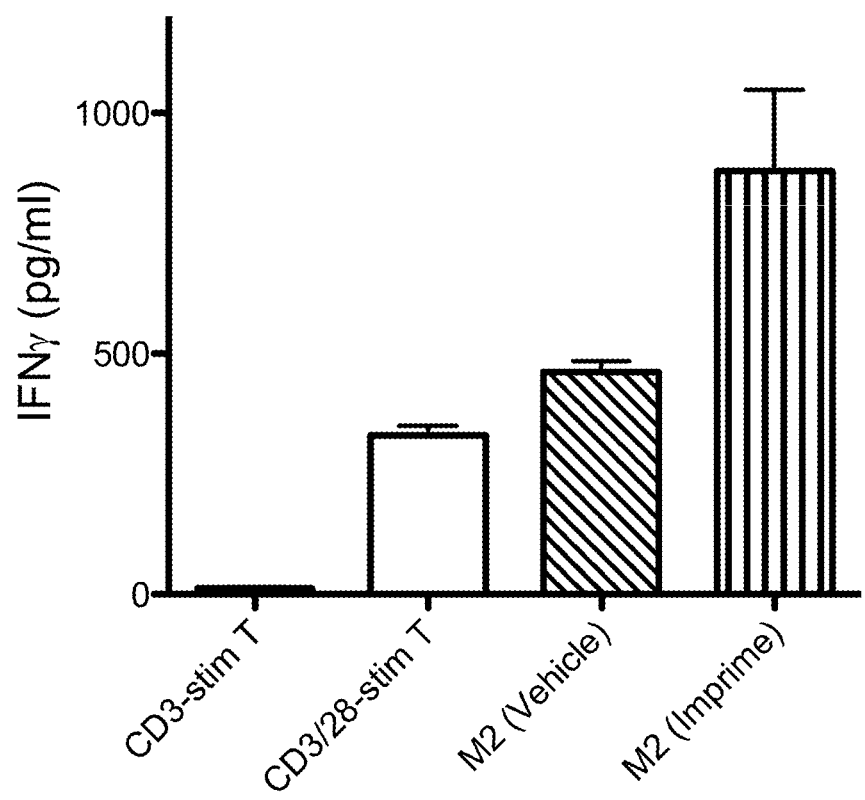

The culture supernatants from the CFSE dilution T-cell proliferation assay (FIG. 2B) were also measured for IFN-gamma levels by ELISA. FIG. 2D is a representative graph of IFN-gamma levels showing a concomitant increase in IFN-gamma production. Thus, β-glucan affects M2 to M1 repolarization and drives anti-tumorigenic Th1 polarization.

Example 3

Effect of β-Glucan on M2 to M1 Repolarization in Cells from High Binding Subjects Vs. Low Binding Subjects:

Early studies evaluating binding of soluble β-glucan to neutrophils and monocytes revealed subjects have different binding capabilities. Further studies found that soluble β-glucan bound to at least some of high binding subjects immune cells, and high binding subjects also had higher levels of natural anti-β-glucan antibodies. Functional studies identified general cutoffs of binding and antibody levels, which were used identify subjects as high binders (high response to β-glucan) and low binders (low response to β-glucan).

Figure 3B:
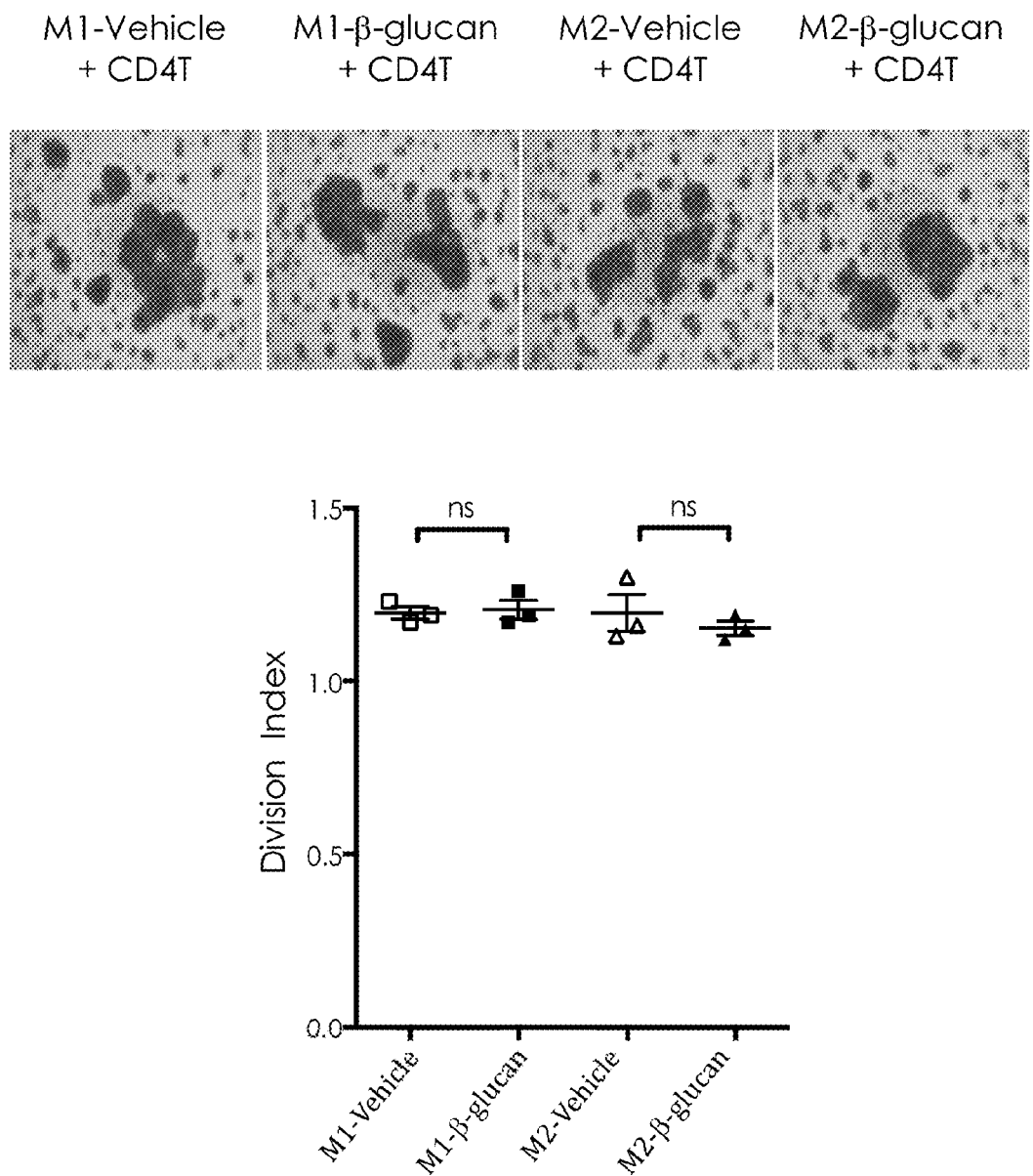

To this end, evaluations of M1/M2 macrophages derived from soluble β-glucan-treated monocytes from high binders and low binders were carried out. M1 and M2 macrophages from high binders and low binders were subsequently evaluated for A) phenotype, B) enhancement of CD4 T cell proliferation and C) modulation of IFN-γ and IL-4 production. FIG. 3A-FIG. 3C are representative results from 4 different experiments.

Expression of a panel of markers was evaluated by flow cytometry for vehicle- and β-glucan-treated, high binder-derived M1 and M2 macrophages (CD163 was evaluated twice). Median MFI was calculated for isotype control staining and surface antigen staining and the results are shown in Table 3.

TABLE 3

| | | High Binder | | | | | | |
|---|---|---|---|---|---|---|---|---|
| | | HLA-DR | CD163 (1) | CD163 (2) | CD206 | CD209 | CD86 | CD274 (PD-L1) |
| M1 | Isotype ctrl | 58 | 58 | 103 | 84 | 98 | 139 | 58 |
| | Vehicle- | 795 | 168 | 205 | 759 | 404 | 2052 | 6130 |
| | β-glucan- | 667 | 158 | 230 | 816 | 318 | 2113 | 5563 |
| M2 | Isotype ctrl | 86 | 86 | 91 | 122 | 104 | 254 | 86 |
| | Vehicle- | 1259 | 2434 | 4079 | 1142 | 1064 | 2273 | 3087 |
| | β-glucan- | 1007 | 759 | 1153 | 1056 | 801 | 2953 | 4427 |

CD163 and CD86 were evaluated by flow cytometry for vehicle- and β-glucan-treated, low binder-derived M1 and M2 macrophages. Median MFI was calculated for isotype control staining and surface antigen staining and the results are shown in Table 4.

TABLE 4

| | Low Binder | | |
|---|---|---|---|
| | | CD163 | CD86 |
| M1 | Isotype ctrl | 58 | 278 |
| | Vehicle- | 162 | 2860 |
| | β-glucan- | 132 | 3179 |
| M2 | Isotype ctrl | 54 | 250 |
| | Vehicle- | 3500 | 2445 |
| | β-glucan- | 3315 | 2284 |

The key result is that β-glucan-treated M2 macrophages had lower expression of CD163, one of the key M2 markers. Interestingly, this result was specific for high binders as expression of CD163 in remained the same between vehicle- and β-glucan-treated M2 macrophages.

Next, the ability of M1/M2 macrophages derived from soluble β-glucan-treated monocytes from high binders and low binders to enhance CD3 & CD28-stimulated CD4 T cell proliferation was evaluated. FIG. 3A shows the results of the CD4 T cell proliferation assay in a high binder while FIG. 3B shows the results in a low binder. β-glucan-treated M2 macrophages had significantly higher ability to enhance CD3 & CD28-stimulated CD4 T cell proliferation in comparison to that observed with the vehicle-treated M2 macrophages in high binders while there was no enhanced proliferation in low binders. In addition, β-glucan-treated M1 macrophages showed no differences in this functional ability as compared to the vehicle-treated M2 macrophages in either high binders or low binders.

Figure 3D:
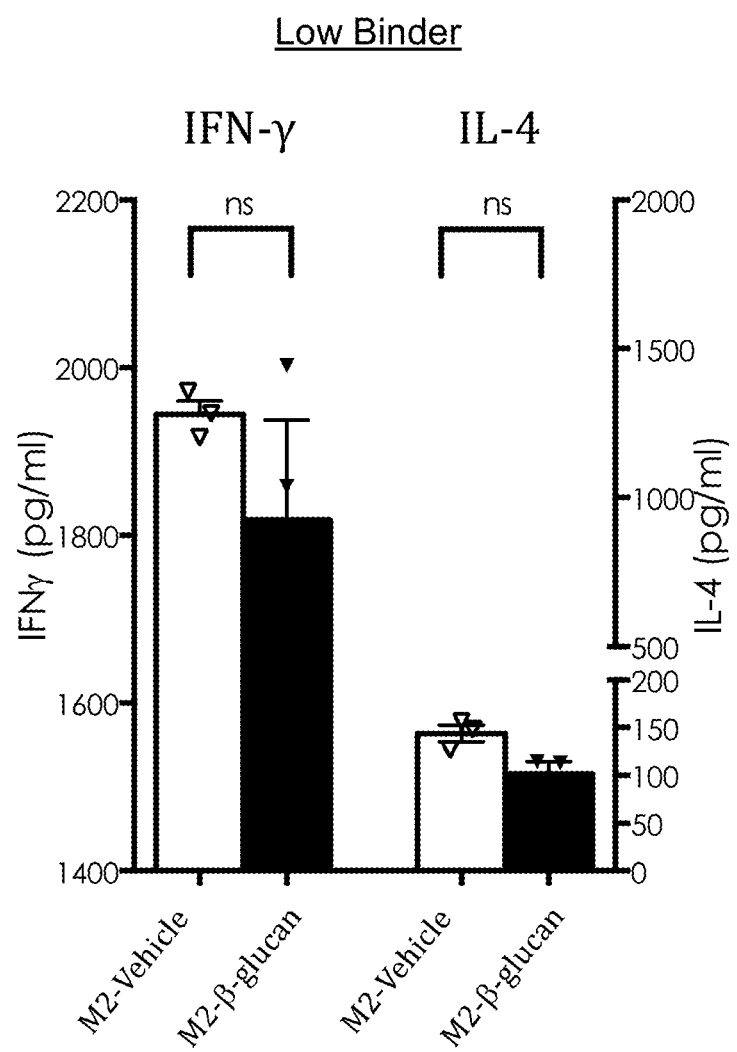

Modulation of IFN-γ and IL-4 production of vehicle- and β-glucan-treated M2 macrophages was then evaluated. Concomitant with enhanced proliferation, significantly increased production IFN-γ, but not IL-4 was observed in co-cultures of β-glucan-treated M2 macrophages and CD4 T cells in high binders (FIG. 3C) but not in low binders (FIG. 3D). Thus, M2 macrophages derived from β-glucan-treated monocytes are M1-like in high binder subjects.

Example 4

Effect of β-Glucan on M2 to M1 Repolarization in Immunosuppressive Conditions:

Phenotypic and functional evaluation of β-glucan-treated M2a and β-glucan-treated M2 macrophages in the presence of immunosuppressive cytokines was carried out. M2 or M2a macrophages were prepared as described above. On day 3, tumor-conditioned medium (TCM) was added M2 macrophage cultures to account for 70% of the volume of the culture and then evaluated for CD163 expression and functional activity on day 6. The TCM from BxPC3, a pancreatic cancer cell line, has been shown to contain several immunosuppressive cytokines including M-CSF, TGF-beta, IL-4, etc. M2a macrophages were cultured in IL-4 as described above.

The β-glucan-treated M2a macrophages cultured in IL-4 and M2 macrophages cultured in TCM were first evaluated for CD163 and CD86 expression. CD163 and CD86 were evaluated by flow cytometry and median MFI was calculated for isotype control staining and surface antigen staining and the results are shown in Table 5.

TABLE 5

| Immunosuppressive conditions | | | |
|---|---|---|---|
| | | CD163 | CD86 |
| M2a | Isotype ctrl | 149 | 147 |
| | Vehicle- | 664 | 4130 |
| | β-glucan- | 309 | 4572 |
| M2 | Isotype ctrl | 138 | 103 |
| | Vehicle- | 1736 | 1283 |
| | β-glucan- | 1112 | 2697 |

As seen in previous M2 differentiation experiments using M-CSF, the β-glucan-treated monocytes cultured in TCM also showed marked down-regulation of CD163. In addition, the β-glucan-treated M2 macrophages had higher HLA-DR expression (data not shown).

Figure 4:
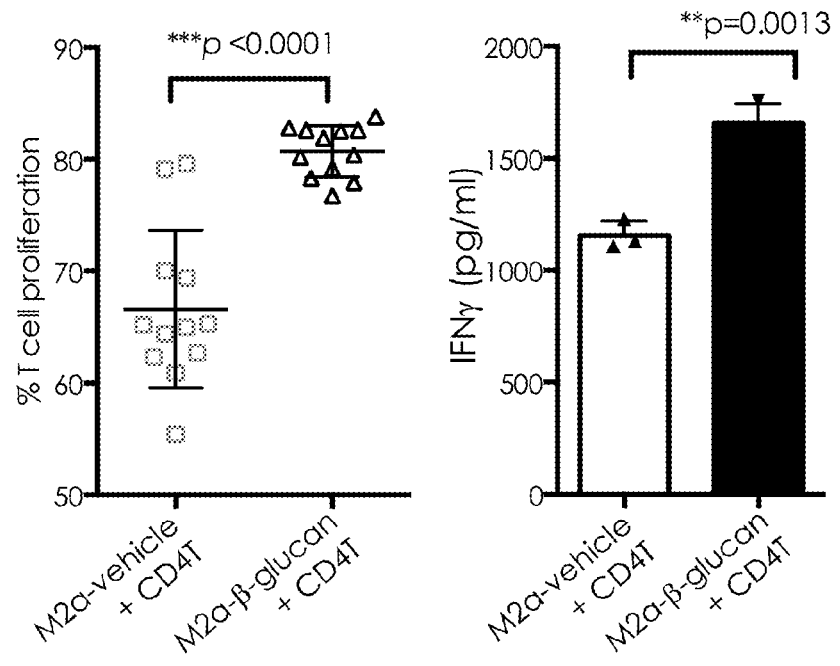
FIG. 4. Evaluations of T cell proliferation and modulation of IFN-γ in β-glucan-treated M2 and M2a macrophages under immunosuppressive conditions.
Figure 4:
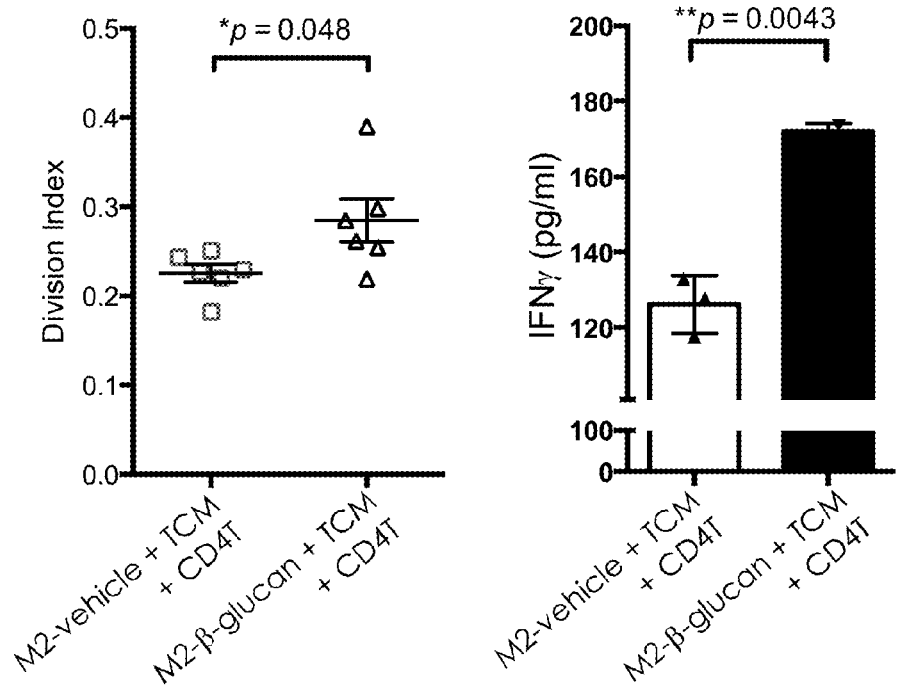

A functional evaluation of ability to modulate CD4 T cell proliferation was then performed by CD4 T cell proliferation assay (three or six replicates in each condition). β-glucan-treated M2 macrophages cultured in TCM and M2a macrophages cultured in IL-4 maintained the ability to enhance CD4 T cell proliferation in comparison to that observed with the vehicle-treated M2 and M2a macrophages. Concomitant with enhanced proliferation, significantly increased production of IFN-γ was observed in co-cultures of macrophages and CD4 T cells (FIG. 4).

The above examples demonstrate that soluble β-glucan has the ability to inhibit M2 polarization and induce more M1-like cells as demonstrated by the reduced expression of CD163, increased expression of CD86, and by inhibiting the ability of M2 to suppress CD4 T cell proliferation. Even under immunosuppressive conditions, simulated by the presence of either IL-4 in combination with M-CSF or tumor conditioned medium (TCM), soluble β-glucan was able to inhibit M2 polarization and enhance their ability to help CD4 T cell proliferation. The enhancement of CD4 T cell proliferation by M2-soluble β-glucan was accompanied with an increase in the pro-inflammatory, Th1 polarizing cytokine, IFN-γ, and no change in the production of immunosuppressive cytokine IL-4.

Example 5

Figure 5A:
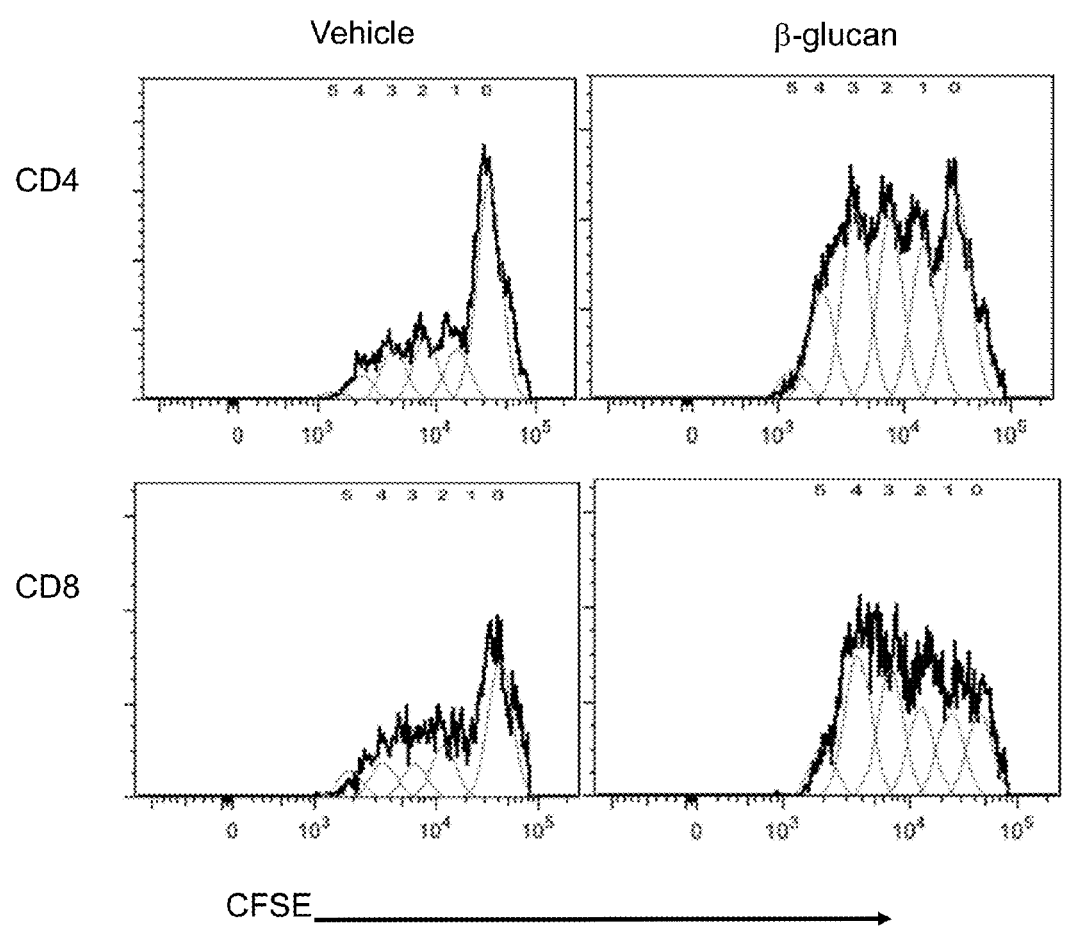
FIG. 5A-5E. Evaluations of β-glucan on CD4/CD8 T cell proliferation and activation in the presence of Tregs.

Effect of β-Glucan on CD4/CD8 T Cell Proliferation and Activation in the Presence of Tregs:

To obtain plasma, whole blood was treated for 6 hours with 25 µg/mL β-glucan or vehicle, spun down and the plasma removed. 50,000 autologous CFSE-labeled PBMCs were cultured in the treated plasma for 3 days in the presence of 50,000 T cell activating CD3/28 beads (DYNABEADS Human T-Activator CD3/CD28 for T Cell Expansion and Activation). At the end of the culture, PBMCs were stained with CD4 and CD8 and T cell proliferation was measured by CFSE dilution. As shown by the representative CFSE dilution plots in FIG. 5A, plasma from β-glucan-treated whole blood provided a significant enhancement in both CD4 and CD8 proliferation as compared to vehicle-treated controls.

Figure 5B:
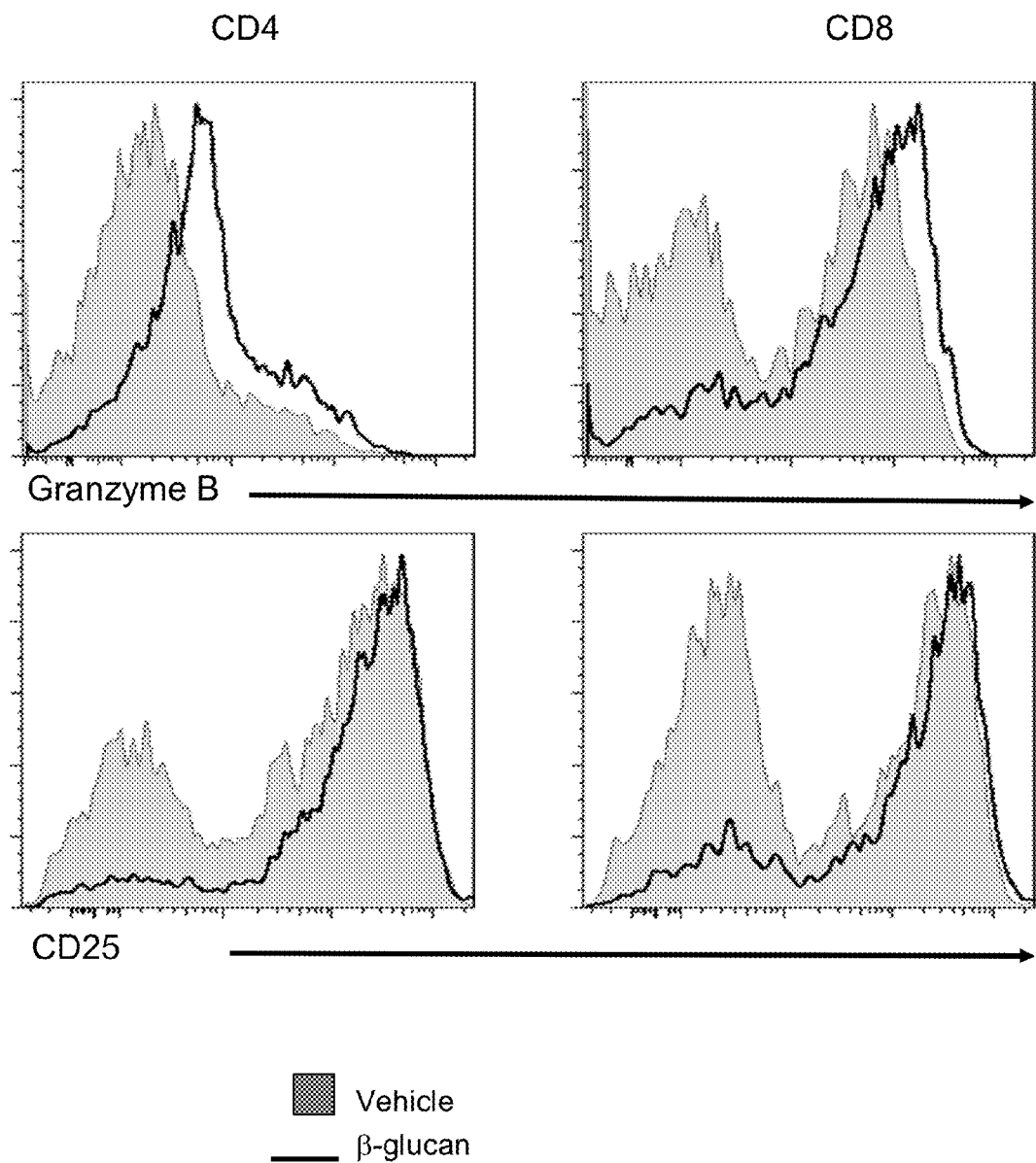

Next, to show the effect of soluble β-glucan on CD4 and CD8 cell activation, the T cell proliferation assay described above was again carried out. At day 3, however, the cells were stained for markers of activation including Granzyme B production and CD25 upregulation. The graphs shown in FIG. 5B demonstrate that β-glucan-treated plasma enhances CD4 and CD8 cell activation.

Figure 5C:
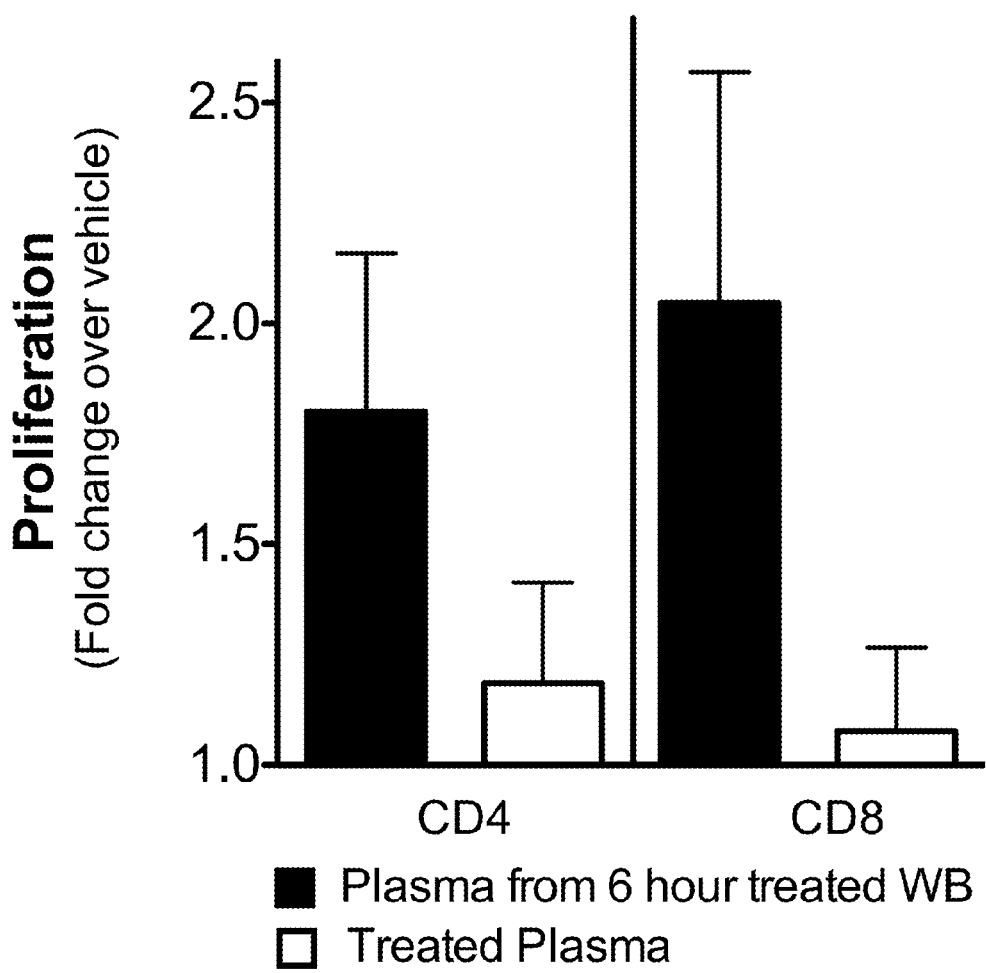

The enhancement in proliferation was greatest when whole blood was treated for the 6 hour incubation period prior to plasma isolation, indicating that this effect on T cell proliferation is the result of an indirect mechanism (i.e. cytokine release by innate immune cells). To determine whether the enhancement of T cell proliferation by β-glucan is direct or indirect, T cell proliferation assays were carried out as described above except the plasma from untreated (vehicle) whole blood was then either treated with β-glucan or vehicle prior to adding to autologous PBMCs. CFSE dilution was quantitated by Division Index using FLOWJO software and plotted as fold change over vehicle control. The results shown in FIG. 5C indicate that β-glucan's enhanced effect is due to indirect mechanisms.

Figure 5D:
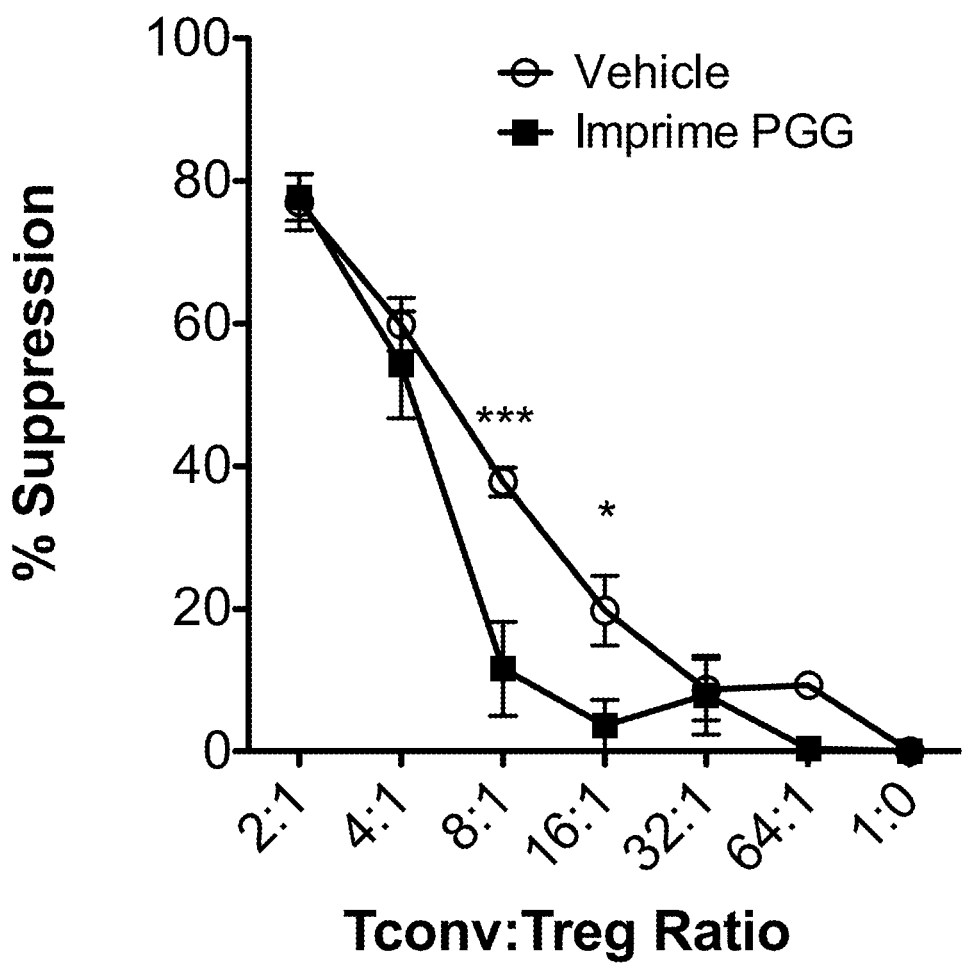

Since these PBMC cultures contain Tregs, the suppressive ability of Tregs seem to be altered in the presence of soluble β-glucan and studies were carried out to determine if β-glucan affected Treg suppression. Plasma from β-glucan-treated or vehicle-treated whole blood (described above) was added to 25,000 isolated CFSE-labeled autologous CD4 T cells (CD4$^+$CD25$^-$) along with increasing numbers of isolated autologous Tregs (CD4$^+$CD25$^+$) resulting in wells with increasing ratios. Cells were then stimulated with 50,000 T cell activating CD3/28 beads for 3 days. Proliferation was subsequently measured by CFSE dilution and quantified by Division Index, which was used to calculate the % suppression of Tregs in the co-culture. % suppression=100−(Division Index of Treg well/Division Index of 1:0 well)/100. The results are shown in FIG. 5D. Plasma from β-glucan-treated whole blood showed significant decreases in the suppressive capacity of Tregs as compared to plasma from vehicle-treated whole blood.

Figure 5E:
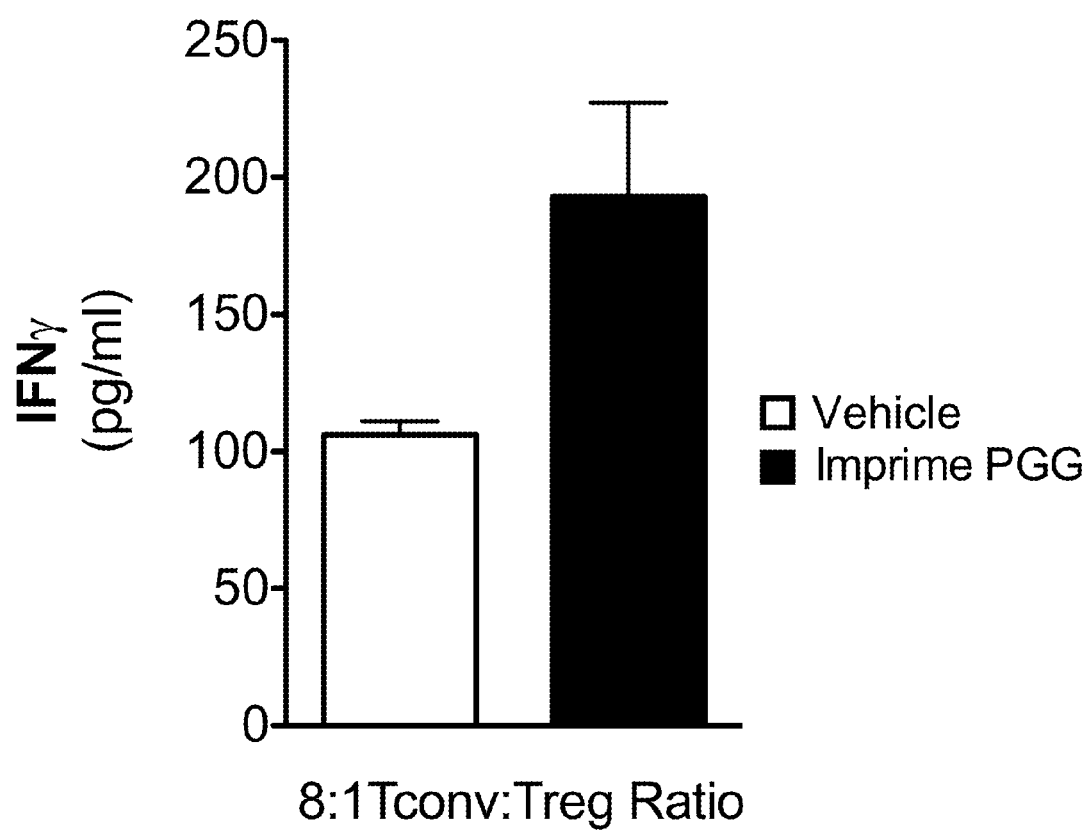

Treg suppression by β-glucan also resulted in enhanced IFN-gamma production. The Treg suppression assay was conducted as described above, and after 3 days of co-culture, supernatants were analyzed for IFN-gamma production. FIG. 5E shows the results of the IFN-gamma production from wells cultured at an 8:1 T cell to Treg ratio. Taken together, these results show that β-glucan affects CD4 and CD8 proliferation along with Treg function resulting in enhanced anti-tumor adaptive effector function.

Example 6

Establishment and Characterization of In Vitro Cultured Human Immature Monocyte-Derived Dendritic Cells (imMoDC) and Mature Monocyte-Derived Dendritic Cells (mMoDC):

Given that macrophages and dendritic cells are the two key antigen presenting cell types that bridge innate and adaptive immunity, the phenotypic and functional effect of soluble β-glucan was also evaluated on human monocyte-derived dendritic cells (MoDC). Monocytes enriched from soluble β-glucan- or vehicle-treated whole blood were cultured in media containing the appropriate cytokines, GM-CSF plus IL-4, for differentiation of dendritic cells. Steps included in the method for in vitro culture and characterization of human MoDCs are outlined below.

Figure 6A:
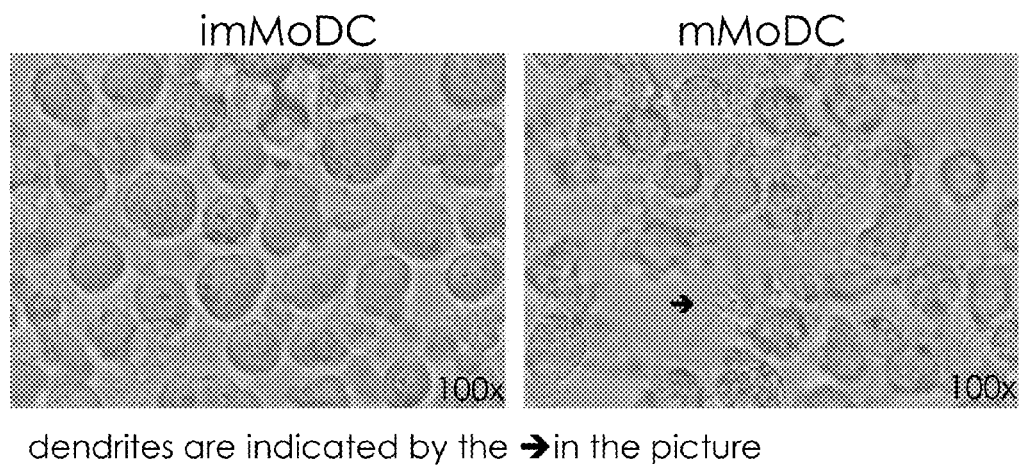
FIG. 6A-6B. Characterization of in vitro cultured human immature monocyte-derived dendritic cells (imMoDC) and mature monocyte-derived dendritic cells (mMoDC).

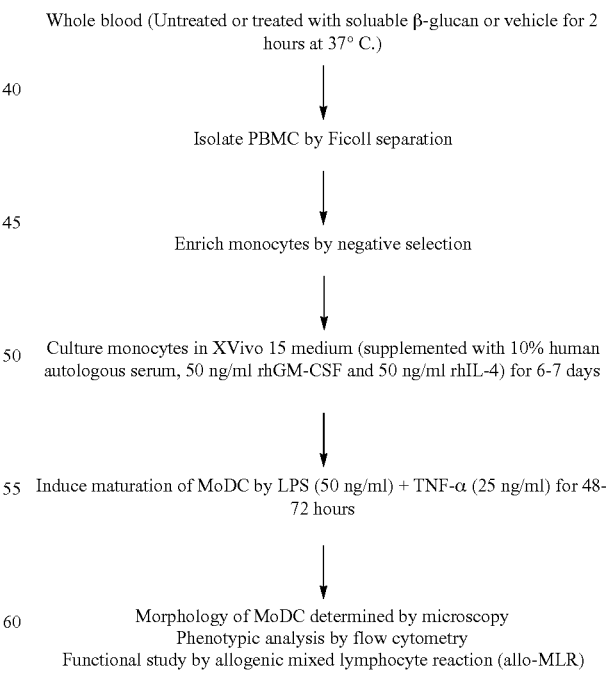

imMoDCs and mMoDCs, prepared as described above, are shown in FIG. 6A. The morphology of mMoDCs is characterized by the presence of long projections or dendrites.

mMoDCs were evaluated for CD80, CD83, CD86 and HLA-DR expression by flow cytometry, and median MFI was calculated for isotype control staining and surface antigen staining and the results are shown in Table 6.

TABLE 6

Figure 6B:
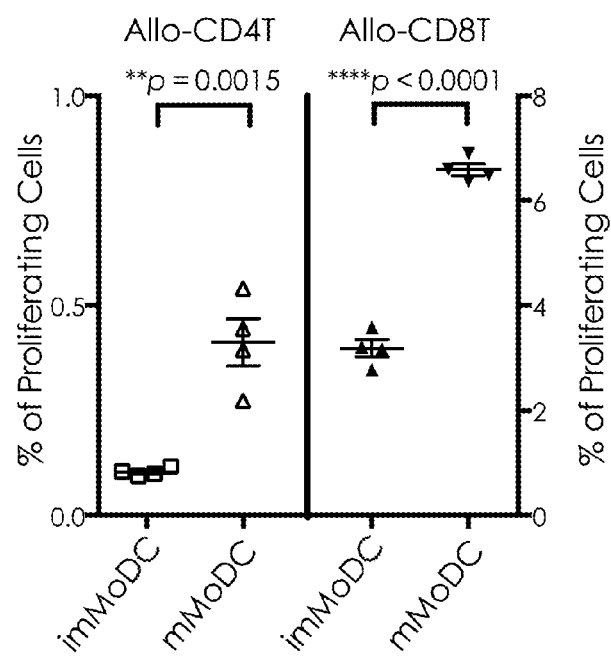

|  |  | CD80 | CD86 | CD83 | HLA-DR |
|---|---|---|---|---|---|
| MoDC | Isotype ctrl | 143 | 93 | 120 | 21 |
|  | imMoDC | 165 | 1554 | 134 | 132 |
|  | m☐☐☐☐ | 492 | 35637 | 448 | 470 | mMoDC showed increased surface expression of the maturation and co-stimulatory markers CD80, CD83, CD86 as well as HLA-DR. Furthermore, these mMoDC also showed immunogenicity in an allogeneic mixed lymphocyte reaction (four replicates in each condition), triggering increased CD4 and CD8 T cell expansion (FIG. 6B).

Example 7

Effect of β-Glucan on Maturation of MoDCs:

The phenotypic and functional evaluation of mMoDC prepared from soluble β-glucan-treated whole blood of a high binder and low binder was carried out. mMoDCs from a high binder and a low binder were prepared as described above. mMoDCs were evaluated for CD80, CD83, CD86 and HLA-DR expression by flow cytometry, and median MFI was calculated for isotype control staining and surface antigen staining and the results are shown in Table 7.

TABLE 7

|  |  | mMoDCs | | | |
|---|---|---|---|---|---|
|  |  | CD80 | CD86 | CD83 | HLA-DR |
| High binder | Isotype ctrl | 223 | 151 | 162 | 151 |
|  | Vehicle- | 640 | 871 | 168 | 4286 |
|  | β-glucan- | 744 | 10759 | 466 | 7049 |
| Low binder | Isotype ctrl | 213 | 141 | 162 | 30 |
|  | Vehicle- | 1056 | 67664 | 2346 | 3561 |
|  | β-glucan- | 1197 | 77749 | 2924 | 2960 |

The increased expression of CD80, CD86, CD83 and HLA-DR on β-glucan-treated mMoDC derived from high binders indicate that these mMoDCs are more mature than those derived from low binders.

Figure 7A:
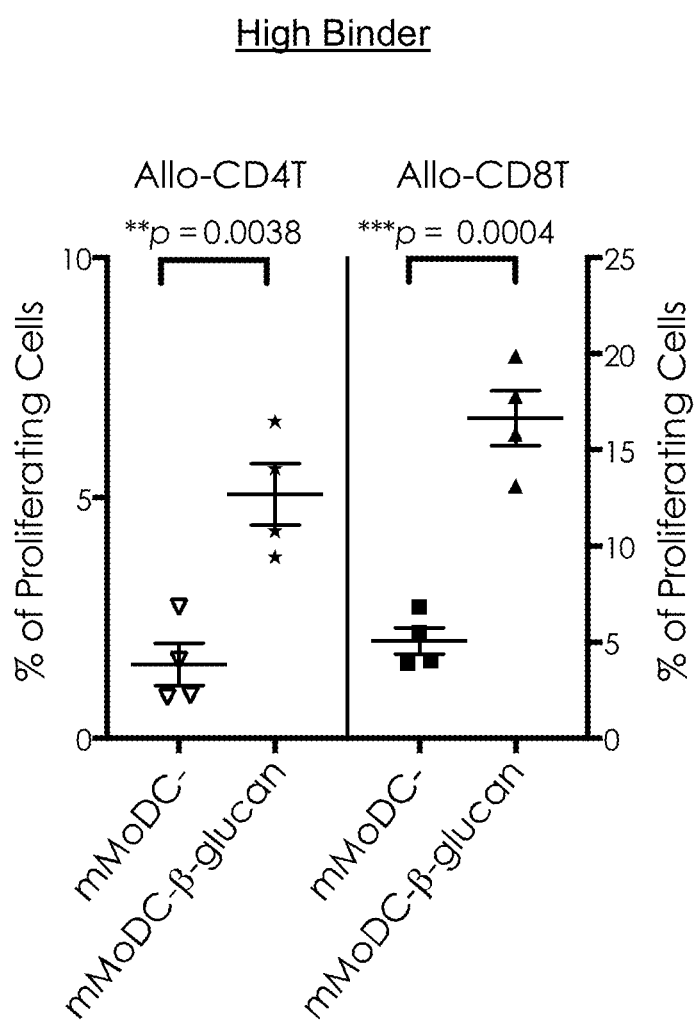
FIG. 7A-7D. Evaluations of β-glucan's effect on MoDCs maturation.
Figure 7B:
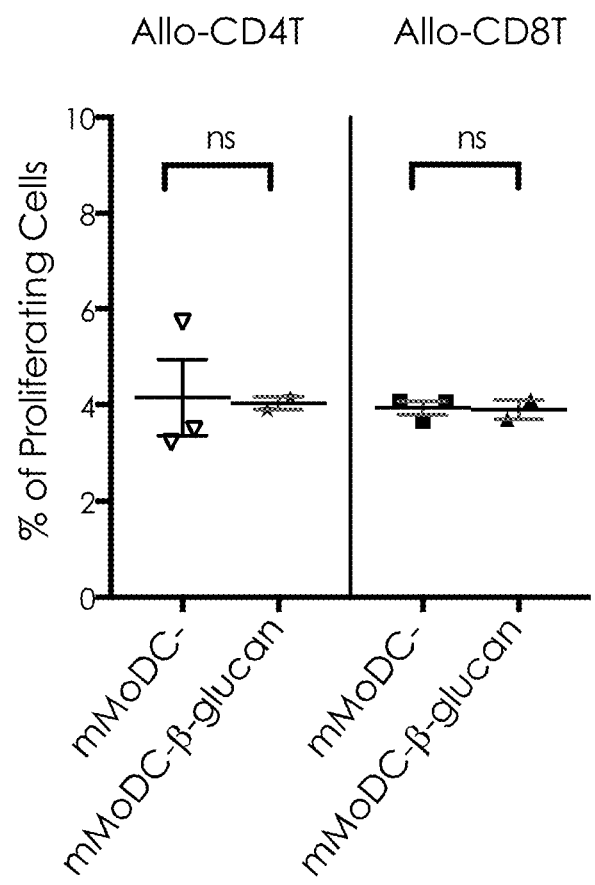

The β-glucan-treated mMoDC derived from high binders also showed increased immunogenicity in an allo-MLR (four replicates in each condition), again triggering increased CD4 and CD8 T cell expansion (FIG. 7A) over cells derived from low binders (FIG. 7B).

Figure 7C:
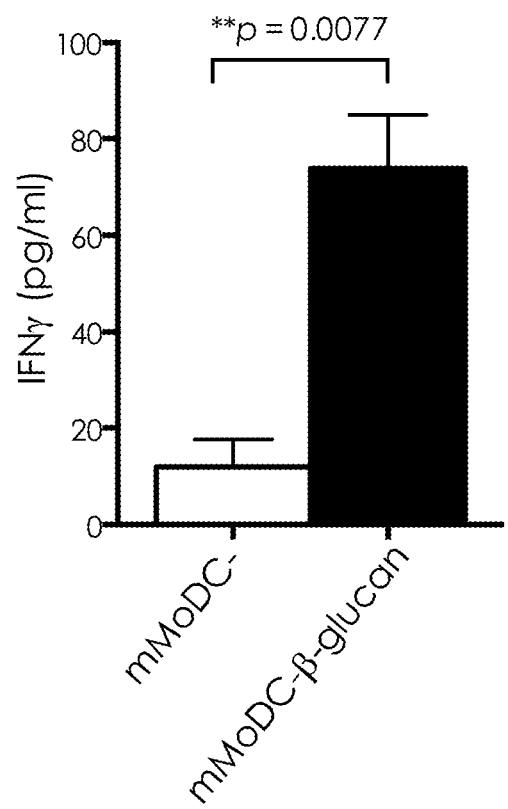
Figure 7D:
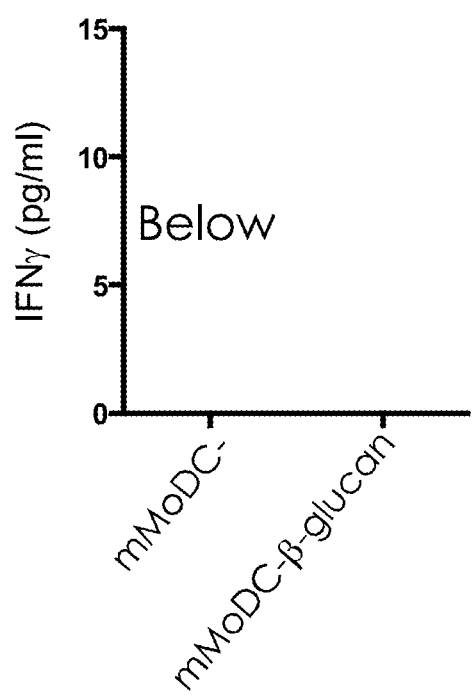

In addition, the β-glucan-treated mMoDC derived from high binders was able to modulate IFN-γ production over cells derived from low binders and vehicle-treated mMoDCs (FIG. 7C).

MoDC derived from β-glucan-treated monocytes are more mature even in immunosuppressive conditions. MoDCs were prepared as described above. TCM was added to account for 70% of the volume of the culture on day 0 and was present throughout the culturing period. mMoDCs cultured in the presence of TCM were subsequently evaluated for phenotypic changes. Median MFI was calculated for isotype control staining and surface antigen staining and results are shown in Table 8.

TABLE 8

| Immunosuppresive Conditions | | | | | |
|---|---|---|---|---|---|
|  |  | CD80 | CD86 | CD83 | HLA-DR |
| MoDC | Isotype ctrl | 120 | 88 | 118 | 31 |
|  | Vehicle- | 439 | 3340 | 274 | 352 |
|  | β-glucan- | 465 | 15797 | 607 | 361 |

Example 8

Cell-to-Cell Contact and Soluble Factors Increase CD4 T Cell Proliferation by β-Glucan-Treated M2 Macrophages:

Using CD4 T cell proliferation as the read-out, the requirement of cell-to-cell contact or soluble factor(s) in initiating the proliferation by β-glucan-treated M2 macrophages was studied. To study cell-to-cell contact between macrophages and T cells, CD4 T cell proliferation was measured when co-cultured with β-glucan-treated M2 macrophages in the absence of CD28 co-stimulation and modulation of surface activation markers was studied on both β-glucan-treated M2 macrophages and T cells in the co-culture.

Evaluation of cell-to-cell contact was carried out as follows: vehicle- and β-glucan-treated M2 macrophages and CD3 & CD28– versus CD3 only-stimulated CD4 T cell co-cultures were utilized for measuring CD4 T cell proliferation and IFN-γ production.

Figure 8B:
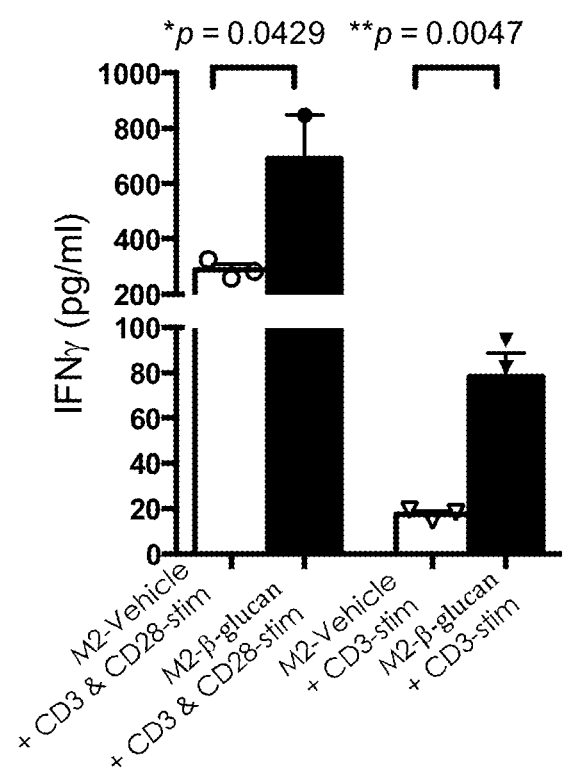

As shown in FIG. 8A, β-glucan-treated M2 macrophages cultured with CD4 T cells in the absence of exogenous CD28 antibody demonstrated significantly higher ability to enhance CD4 T cell proliferation. Concomitant with enhanced proliferation, significantly increased production of IFN-γ was observed in co-cultures of β-glucan-treated M2 macrophages and CD4 T cells (FIG. 8B).

Figure 8C:
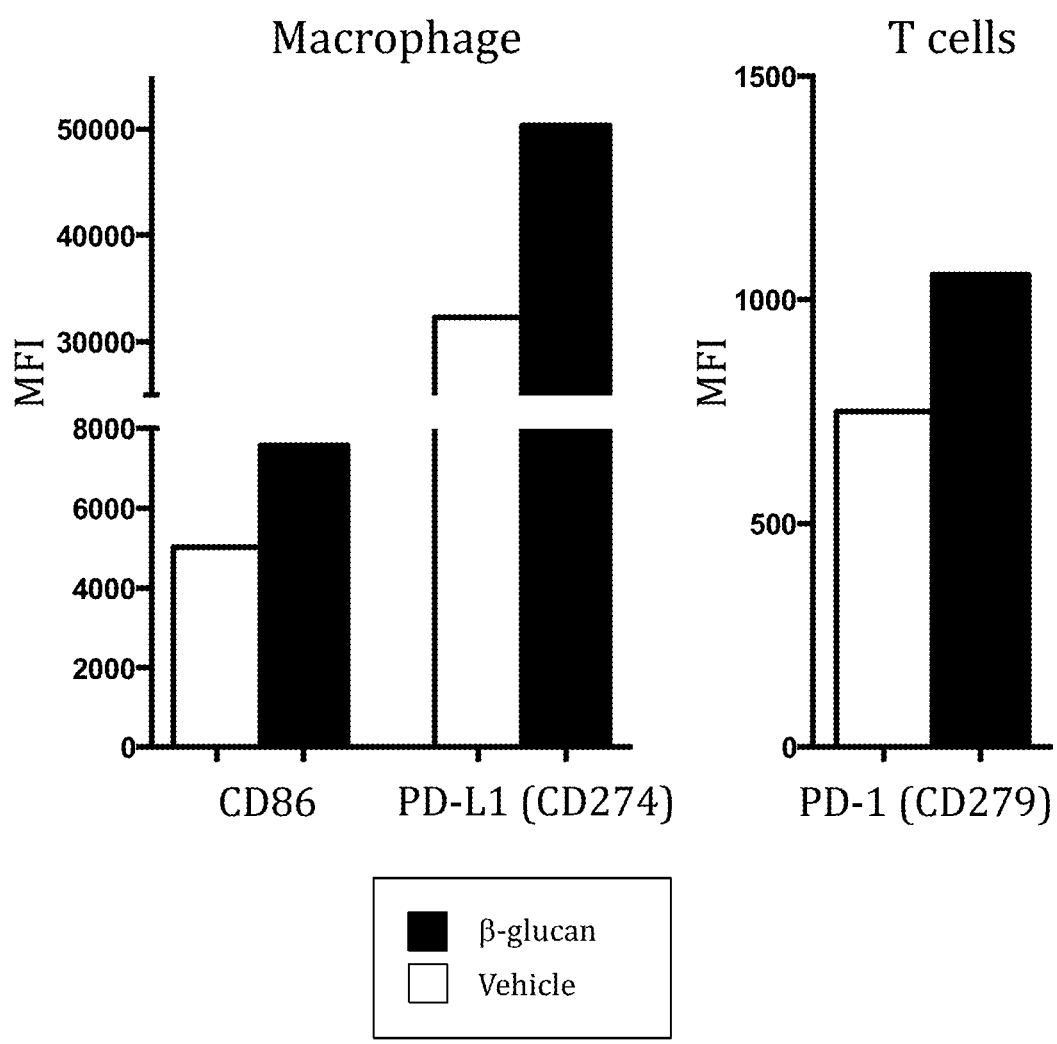

Changes in surface marker expression on both macrophages and CD3 & CD28-stimulated T cells were also measured. Vehicle- and β-glucan-treated M2 macrophages and CD T cells from the co-cultures were evaluated by flow cytometry for the modulation of co-stimulatory or co-inhibitory molecules. FIG. 8C and Table 9 are representative results from 2 different experiments.

TABLE 9

| Surface Markers | Change in MFI on Macrophages* | Change in MFI on T cells* |
|---|---|---|
| HLA-DR | No change | NA |
| CD86 | Increase | NA |
| CD80 | No change | NA |
| CD28 | NA | No change |
| CTLA-4 | NA | No change |
| CD40 | No change | NA |
| CD40L | NA | No change |
| 4-1BBL | No change | NA |
| 4-1BB | NA | No change |
| OX40 | No change | NA |
| PD1 (CD279) | NA | Increase |
| PD-L1 (CD274) | Increase | NA |
| CD209 | No change | NA |
| CD172 | No change | NA |

*Change in MFI on β-glucan-treated M2 macrophages/T cells relative to that observed in vehicle-treated M2 macrophages/T cells Of all the surface markers tested, a relative increase in surface expression of CD86 (day 8) and PD-L1 (day 9) was observed on the surface of β-glucan-treated M2 macrophages as compared to that on the vehicle-treated M2 macrophages. Increased expression of PD-1 (day 9) was observed on the surface of T cells co-cultured with β-glucan-treated M2 macrophages.

Figure 9:
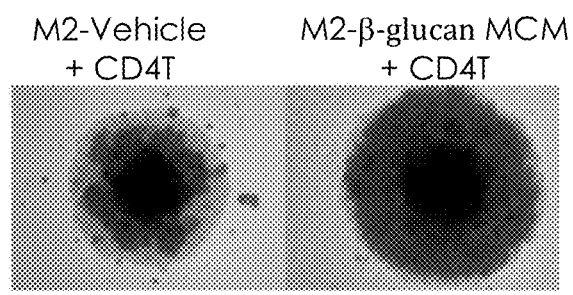
FIG. 9. Results of increased CD4 T cell proliferation by M2-β-glucan due to soluble factors.
Figure 9:
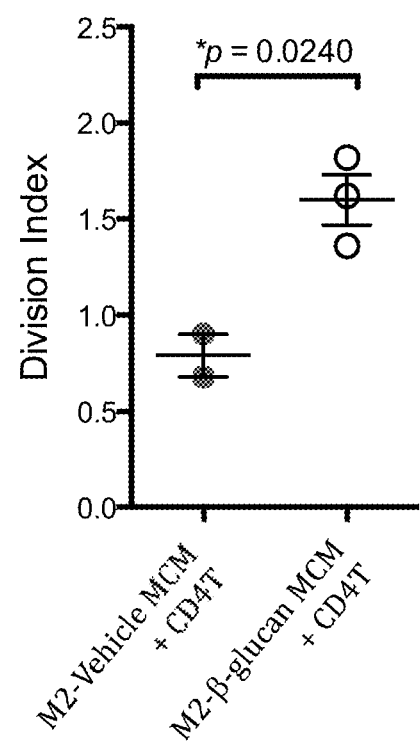

To determine whether soluble factors secreted from β-glucan-treated M2 macrophages are required, measurements were carried out of CD4 T cell proliferation co-cultured with β-glucan-treated M2 macrophages MCM (50% of volume) and surface activation marker modulation on T cells incubated with the MCM were observed. FIG. 9 is representative of 2 different experiments. When evaluated by CD4 T cell proliferation assay, β-glucan-treated M2 macrophage MCM cultured with CD4 T cells demonstrated significantly higher ability to enhance CD4 T cell proliferation (FIG. 9) in comparison to the vehicle-treated M2 macrophage MCM. In addition, the CD4 T cells cultured in vehicle- and β-glucan-treated M2 macrophage MCM were evaluated for modulation of co-stimulatory or co-inhibitory molecules (CD80, CD28, CTLA-4, 4-1BB and PD-1). Surprisingly, no change in any of the T cell markers was observed (data not shown).

Example 9

Analysis of β-Glucan-Treated M2 Macrophages in High Binders Vs. Low Binders:

As discussed previously, anti-β-glucan antibody (ABA) thresholds in subjects have been shown to be important for β-glucan immunotherapy. Therefore, the importance of ABA threshold in β-glucan's ability to modulate M1/M2 polarization was investigated. β-glucan's ability to modulate M1/M2 polarization in high binders versus low binders was determined by both phenotypic and functional evaluations.

Figure 10:
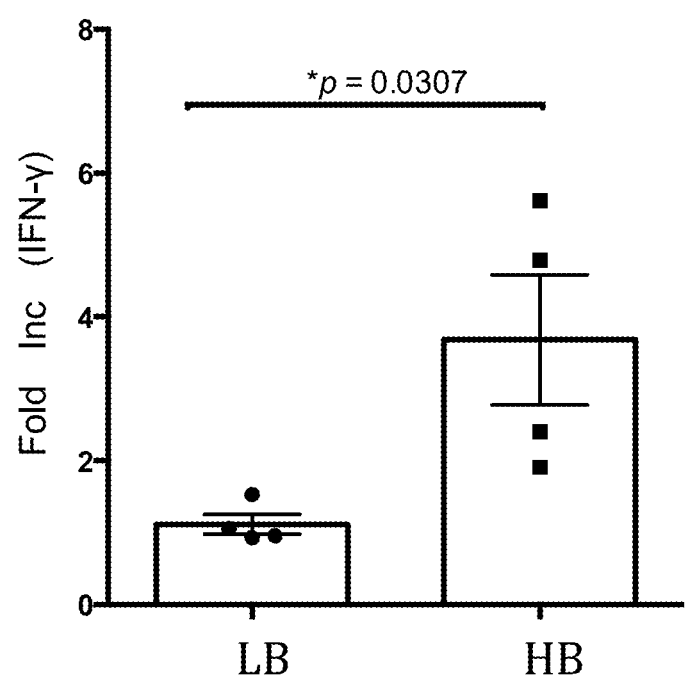
FIG. 10. Analysis of β-glucan-treated M2 macrophages in high binders vs. low binders.

M2 macrophages from 4 high binders and 4 low binders were prepared and evaluated for their ability to modulate CD4 T cell proliferation. The supernatants from the various CD4 T cell proliferation conditions were measured for IFN-γ by ELISA. Results shown in FIG. 10 are representative from 4 different experiments. Fold change over the IFN-γ levels produced in the co-cultures of vehicle-treated M2 macrophages and CD4 T cells are plotted for each of the 4 donors.

In low binders, β-glucan did not modulate any of the phenotypic markers on the monocyte-derived macrophages in M1/M2 polarizing conditions (data not shown), and in a functional evaluation of low binders by CD4 T cell proliferation assay, the β-glucan-treated M2 macrophages neither enhanced CD4 T cell proliferation nor increased IFN-γ production.

Example 10

Serum Cross-Over Studies:

Because β-glucan failed to show modulation of M1/M2 polarization in low binders, modulation by β-glucan using monocytes from a low binder in the presence of serum containing higher levels of ABA (serum cross-over from a high binder) was evaluated. To test this, M2 macrophages were prepared as described above with a few modifications. The whole blood of a low binder was spun down to remove the plasma and then the cells were reconstituted with serum obtained from a high binder. The reconstituted blood was treated with vehicle or β-glucan (25 µg/mL) for 2 hours at 37° C. The monocytes were evaluated for binding by using anti-β-glucan specific monoclonal antibody and subsequent flow cytometry. The vehicle- or β-glucan-treated monocytes in whole blood were then isolated and differentiated to M2 macrophages, and either the M2 cells (data not shown) or the MCM were used to evaluate for their ability to enhance CD4 T cell proliferation (six replicates in each condition) and increase IFN-γ production using methods described above.

Figure 11A:
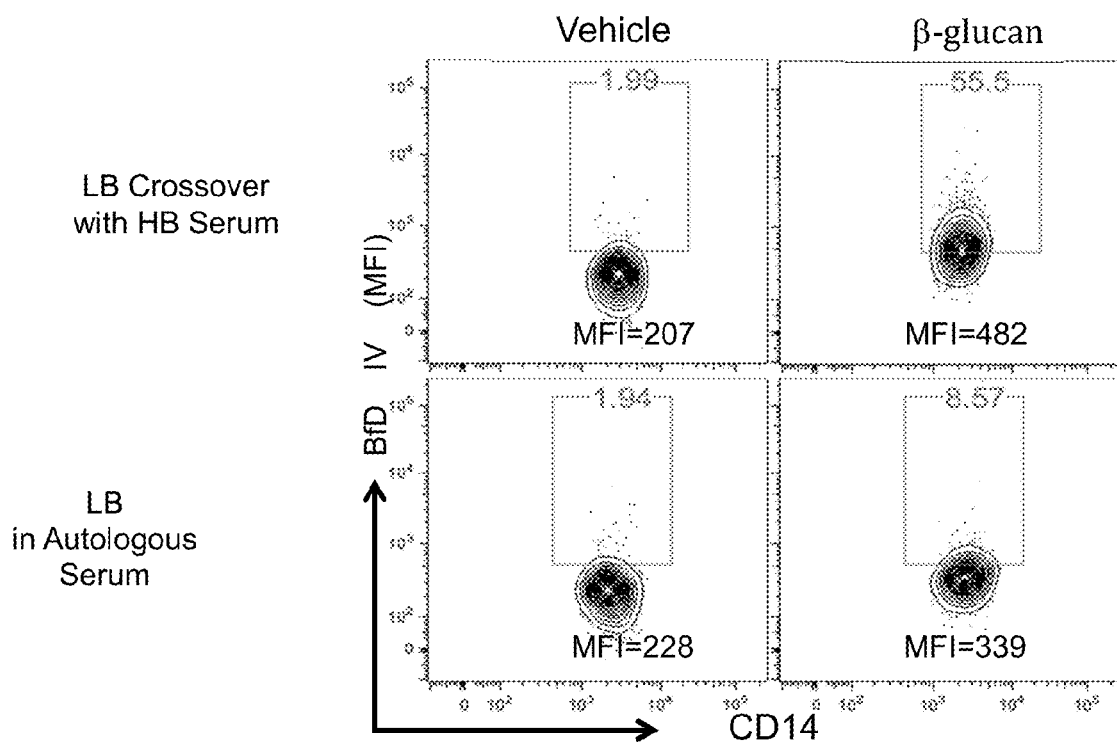
FIG. 11A-11B. Results of the functional evaluation of M2-β-glucan derived from low binders's monocytes in the presence of serum from a high binder.
Figure 11B:
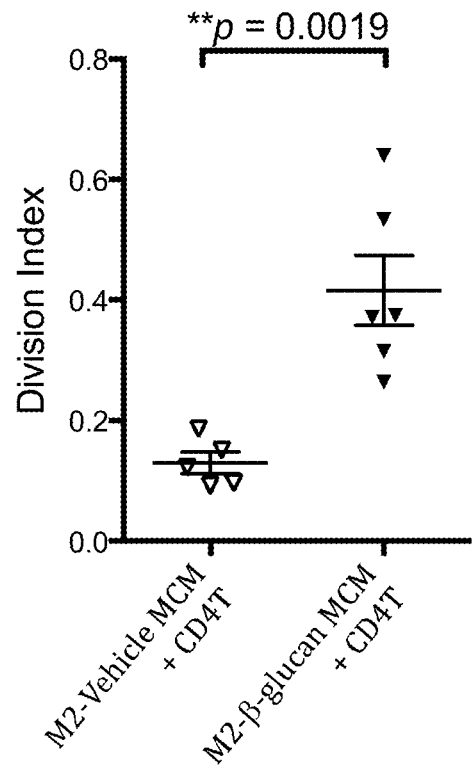
Figure 11B:
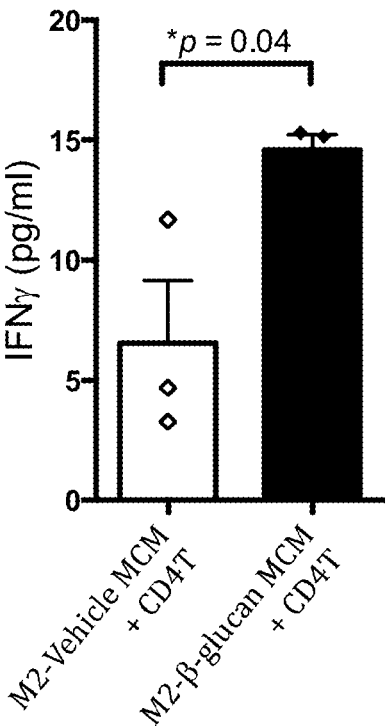

Monocytes in the whole blood of a low binder did not bind β-glucan but showed significantly higher binding when a high binder's serum containing higher levels of ABA was added to the low binder's whole blood (FIG. 11A). In addition, MCM from β-glucan-treated M2 macrophages of a low binder crossed-over with a high binder's serum have significantly higher ability to enhance CD4 T cell proliferation in comparison to that observed with the vehicle-treated M2 macrophages. Concomitant with enhanced proliferation, significantly increased production of IFN-γ was observed in co-cultures of β-glucan-treated M2 macrophage and CD4 T cells (FIG. 11B).

Example 11

Figure 12A:
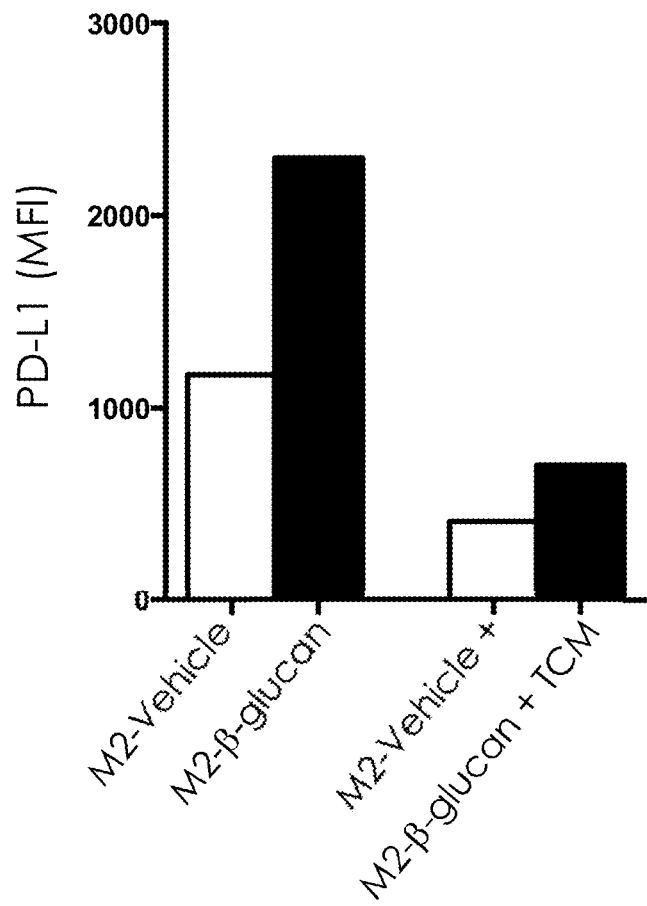
FIG. 12A-12B. PD-L1 upregulation on β-glucan-treated M2 macrophages cultured in the presence of immunosuppresive cytokines (TCM).
Figure 12A:
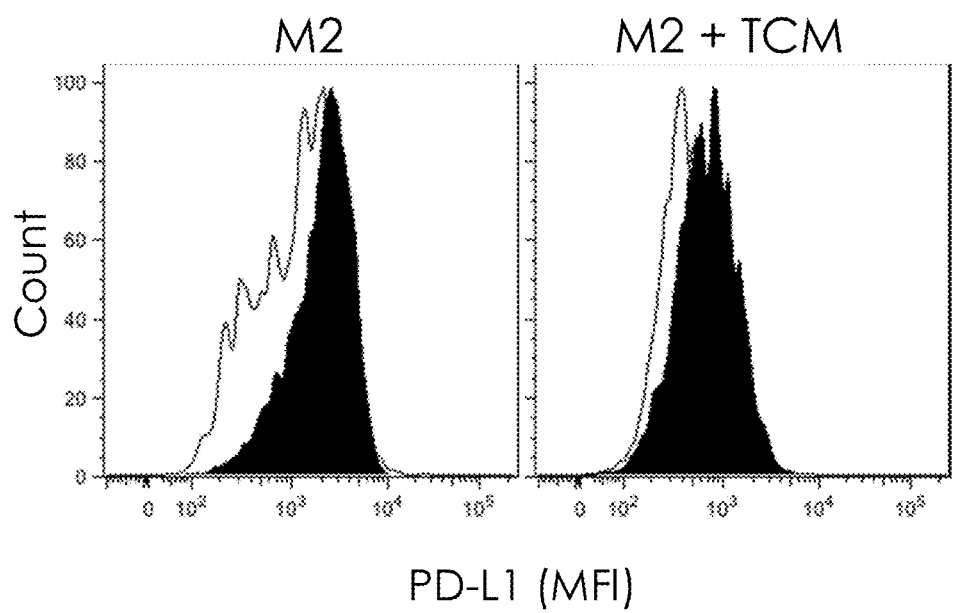
Figure 12B:
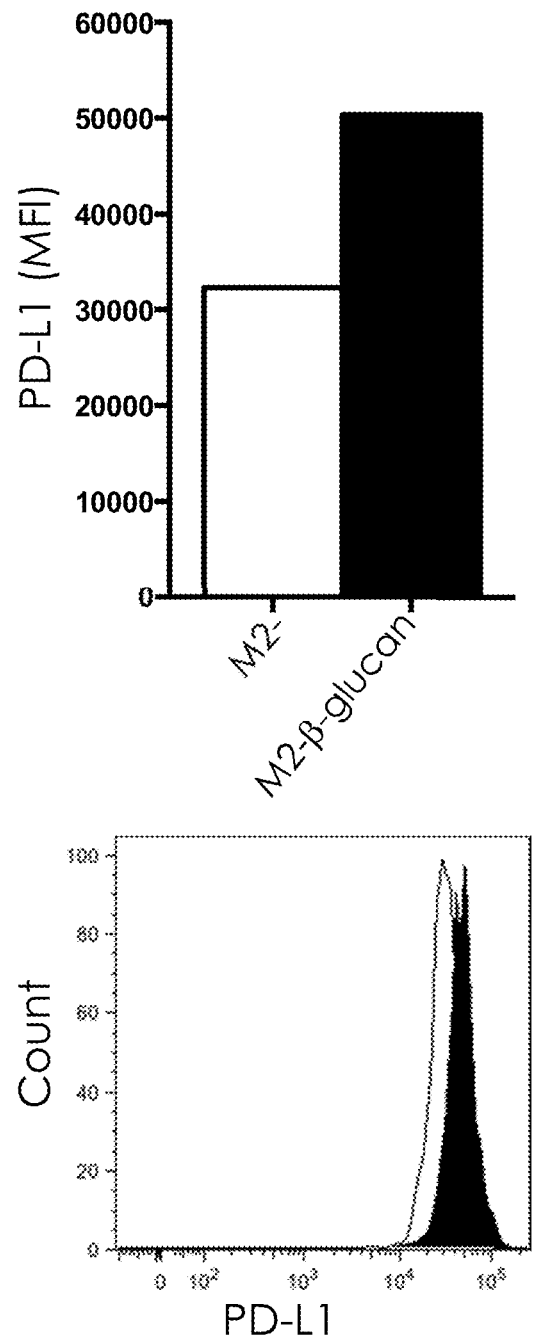

PD-L1 Upregulation on β-Glucan-Treated M2 Macrophages Cultured in the Presence of Immunosuppressive Cytokines (TCM):

Monocytes or M2 macrophages were prepared as described above. On day 3, TCM was added to account for 70% of the volume of the culture and then evaluated for PD-L1 expression with TCM and then again when co-cultured with CD4 T cells.

β-glucan-treated M2 macrophages cultured in the TCM had higher surface expression of PD-L1 (FIG. 12A). There was also increased expression when co-cultured with CD4 T cells (FIG. 12B).

Using the above system, it was determined that β-glucan has the ability to inhibit M2 polarization as demonstrated by the reduced expression of a key M2 marker, CD163, and by inhibiting the ability of M2 to suppress CD4 T cell proliferation. Even under an immunosuppressive environment, stimulated by the presence of either IL-4 in combination with M-CSF (data not shown) or tumor-conditioned medium (TCM), β-glucan was able to inhibit M2 polarization and enhance their ability to help CD4 T cell proliferation. The enhancement of CD4 T cell proliferation by M2-β-glucan was accompanied with an increase in the pro-inflammatory, Th1 polarizing cytokine, IFN-γ, and no change in the production of immunosuppressive cytokine IL-4. As expected with increased T cell activation and IFN-γ production, increases in surface expression of PD-L1 on β-glucan-treated M2 macrophages and PD-1 on T cells were observed. The β-glucan-treated M2 macrophages themselves, as well as the soluble factors secreted by the cells are important for enhancing CD4 T cell proliferation. Lastly, β-glucan inhibited M2 polarization in only the cells from healthy donors having higher levels of ABA.

Example 12

Figure 13:
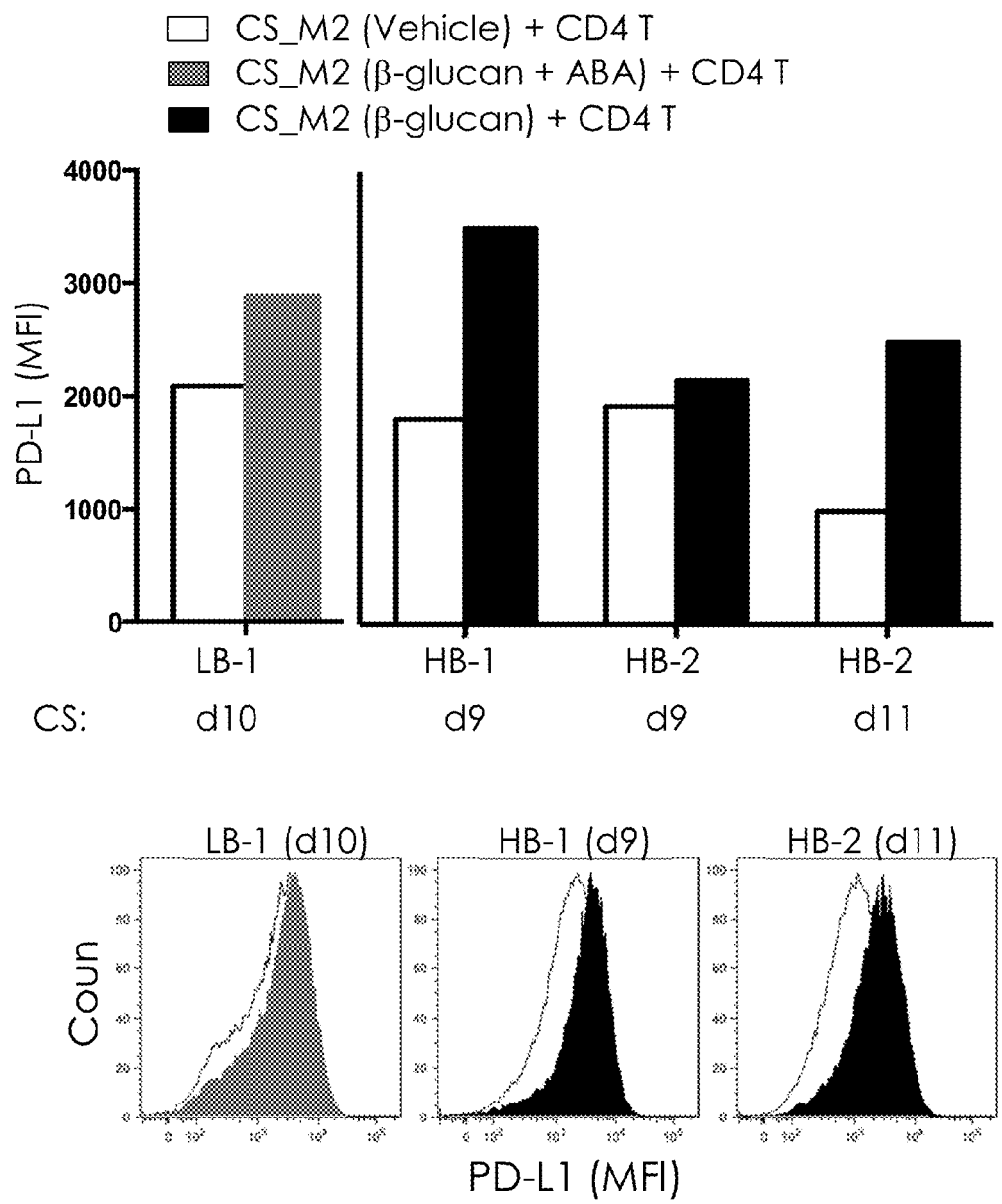
FIG. 13. PD-L1 upregulation in MiaPaCa.

PD-L1 Upregulation in MiaPaCa:

β-glucan- and vehicle-treated M2 macrophages and β-glucan-treated M2 macrophages+ABA were cultured with high binder serum and low binder serum to evaluate PD-L1 expression on tumor cells. FIG. 13 shows that β-glucan-treated M2 macrophages increased expression of PD-L1 on tumor cells in high binders, and with addition of ABA, β-glucan-treated M2 macrophages also increased expression of PD-L1 on tumor cells in low binders.

Example 13

Effect of Soluble β-Glucan on Myeloid-Derived Suppressor Cells (MDSC):

MDSC accumulate in the blood, lymph nodes, and bone marrow and at tumor sites in most patients and experimental animals with cancer and inhibit both adaptive and innate immunity. MDSC are induced by tumor-secreted and host-secreted factors, many of which are pro-inflammatory molecules. The induction of MDSC by proinflammatory mediators led to the hypothesis that inflammation promotes the accumulation of MDSC that down-regulate immune surveillance and antitumor immunity, thereby facilitating tumor growth.

Figure 14A:
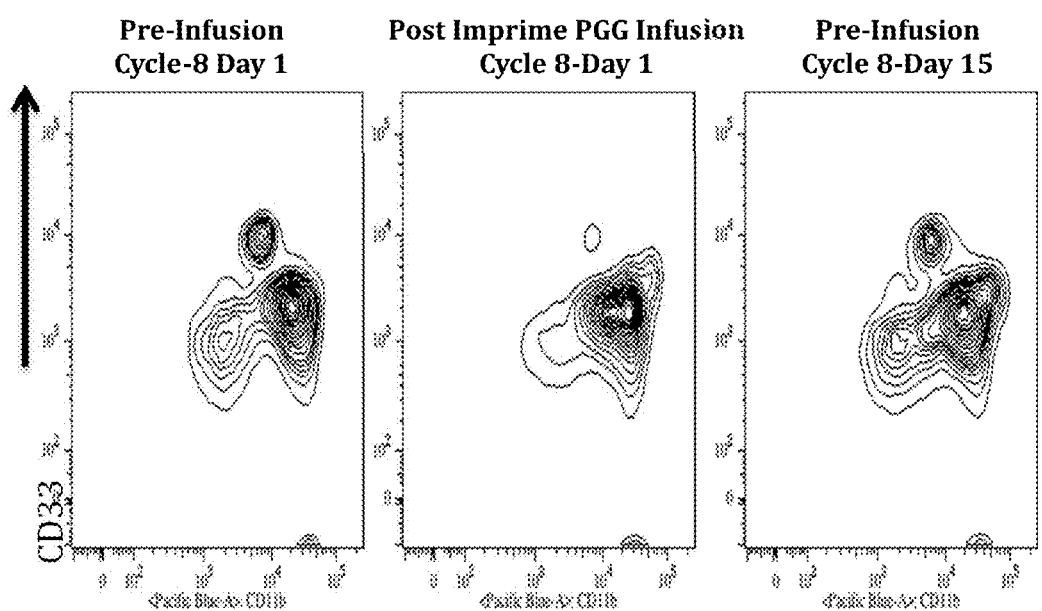
FIG. 14A-14B. Effects of soluble β-glucan on myeloid-derived suppressor cells (MDSC).

Blood was drawn at various times from a case study subject undergoing treatment with IMPRIME PGG and analyzed for the presence of MDSC. The first blood draw was done pre-infusion, cycle 8, day 1. As shown in FIG. 14A, a large population of $CD33^+$, MDSC are present in peripheral blood. A second blood draw was done post-infusion, cycle 8, day 1. As shown in the second panel of FIG. 14A, within hours post-infusion the MDSC transiently disappear. The last blood sample was drawn pre-infusion, cycle 8, day 15. The $CD33^+$ MDSC are again present in the peripheral blood.

Figure 14B:
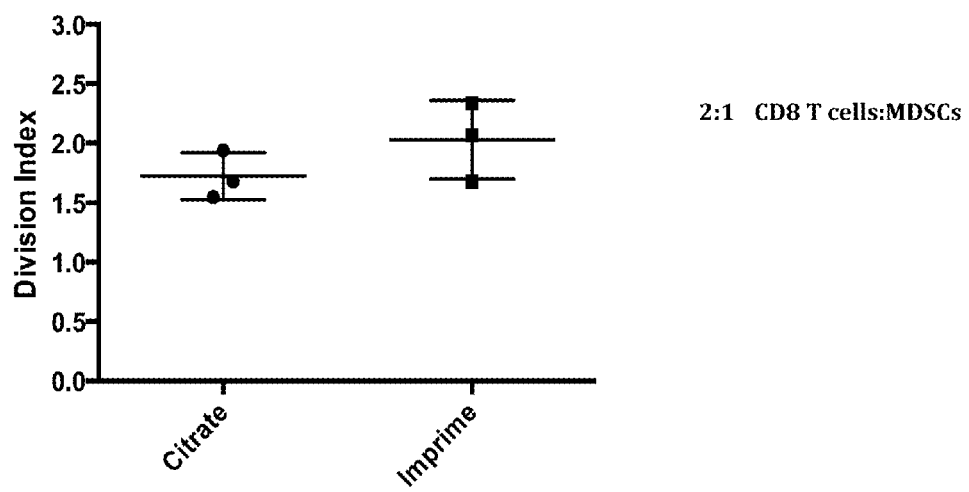

In another study, human cord blood was enriched for $CD34^+$ cells and cultured for 9 days to produce $CD33^+$ $CD11b^+$ cells (MDSC). The MDSC were then treated with soluble β-glucan or citrate buffer (control) and evaluated for their ability to suppress T cell proliferation. The T cell proliferation assay was carried out at a 2:1 ratio of CD8 T cells to treated or untreated MDSCs. As shown in FIG. 14B, β-glucan-treated MDSC were less suppressive to T cell proliferation.

These results indicate that β-glucan modulates the MDSC population making them transiently leave the peripheral blood circulation and less suppressive to T cell proliferation. Thus, if one or more cancer immunotherapeutic drugs or chemotherapeutic drugs are administered in combination with soluble β-glucan, especially during the period of transiently loss of the $CD33^+$ cell population, the therapies would be more effective against the tumors.

Example 14

Figure 15:
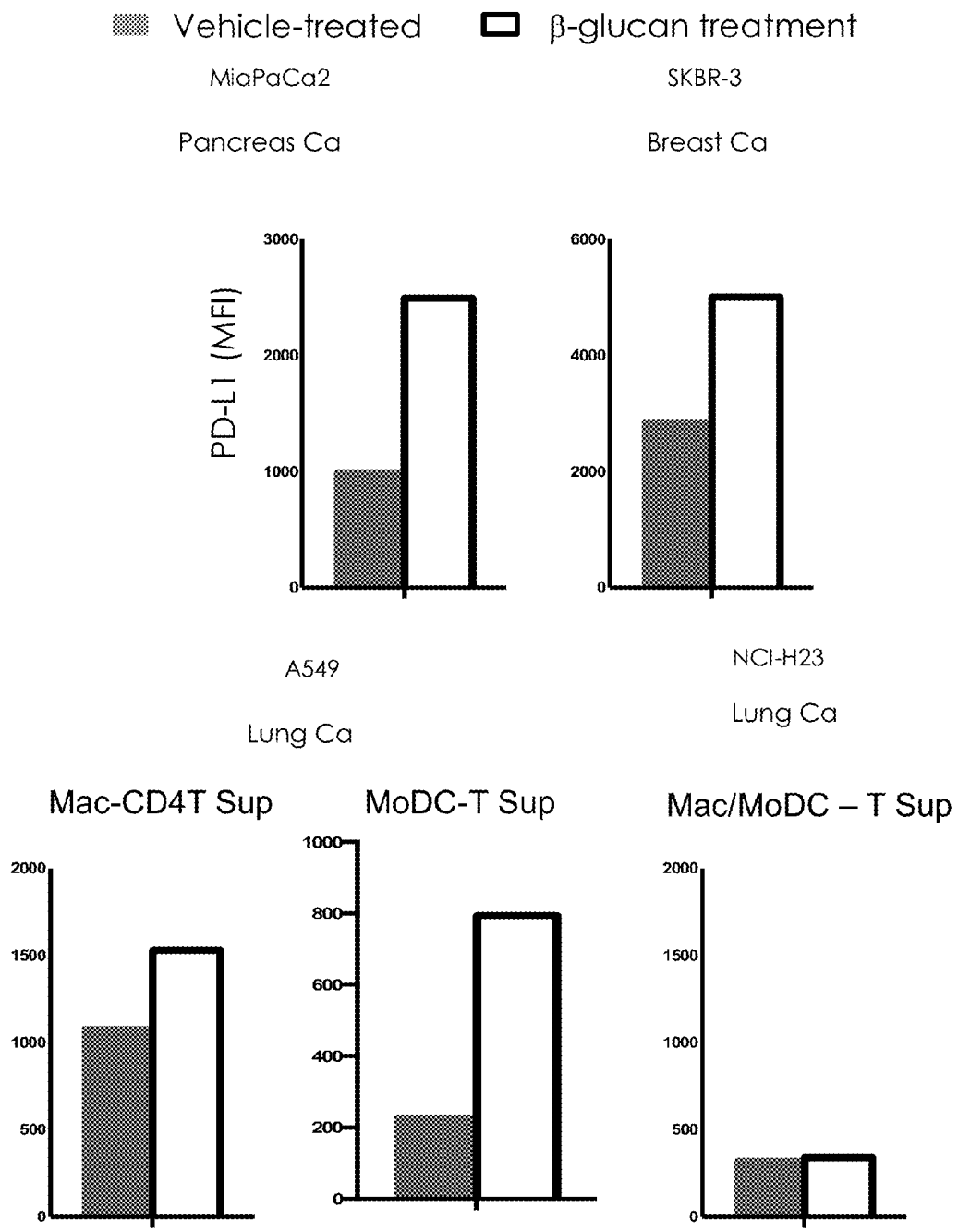
FIG. 15. Evaluation of β-glucan induced PD-L1 expression on tumor cells.

Supernatant from β-Glucan-Treated M2 Macrophages/MoDC and T Cell Co-Culture Induces PD-L1 Expression on Tumor Cells:

M2 macrophages and MoDC were prepared as described above. The macrophages and the MoDC were subsequently used in T cell proliferation assays as described previously. The supernatants from these proliferation assays were harvested and incubated with various tumor cell lines, including NSCLC, breast, pancreatic, colon, and B cell lymphoma. The expression of PD-L1 on these tumor cell lines were evaluated post 48 hours by flow cytometry. Shown in FIG. 15 are representative results from 3 different experiments.

T cells require three signals for their effector mechanisms. Signal 1 is the antigen presented in the context of MEW molecules on the antigen presenting cells (APC), signal 2 is provided by the membrane costimulatory molecules on the APC, and signal 3 is the cytokines produced in the milieu for effector function. Coinhibitory molecules, such as PD-L1 can inhibit the effector functions of T cells.

Macrophages and dendritic cells derived from β-glucan-treated monocytes in vitro have higher expression levels of PD-L1, but the treatment also increases the expression of the costimulatory molecule CD86, (signal 2), and cytokines (signal 3) allowing for enhanced T cell effector function.

The broader, innate and adaptive immune response elicited by β-glucan also enhances PD-L1 expression on the tumor cell lines. These results demonstrate that the up regulation of PD-L1 expression induced by β-glucan on both the immune and the tumor cells makes it a promising combination partner with the checkpoint inhibitor cancer immunotherapy.

It is equally important to note that β-glucan also has the capability to offset the inhibitory effect of PD-L1 up regulation by compensatory mechanisms such as increased expression of costimulatory molecules and production of immunostimulatory cytokines.

Example 15

Effect of Soluble β-Glucan in Combination with Anti-Angiogenic Agents on the TME:

Tumor angiogenesis alters immune function in the TME resulting in an immunosuppressive environment. Anti-angiogenic agents, such as anti-VEGFR2 antibody DC101 (mouse ramucirumab), have proven useful in cancer therapy. Because soluble β-glucan can skew the TME to a more anti-tumor environment, it was used in combination with DC101 to treat NCI-H441 non-small cell lung cancer (NSCLC) subcutaneous xenografts in mice to increase the effectiveness of the DC101 antibody.

6 to 8 week-old female athymic nude mice were injected with $5 \times 10^6$ H441 tumor cells in a volume of 0.2 ml subcutaneously in the flank. Mice were dosed biweekly when the mean tumor volume reached about 150 $mm^3$ with the following agents:
  0.2 ml/mouse vehicle
  1.2 mg/mouse IMPRIME PGG (Biothera, Inc.)
  10 mg/kg or 20 mg/kg DC101 (Clone: DC101 Catalog#: BE0060)

Blood samples were collected on day 10 and 2 hours after the last dose.

Figure 16:
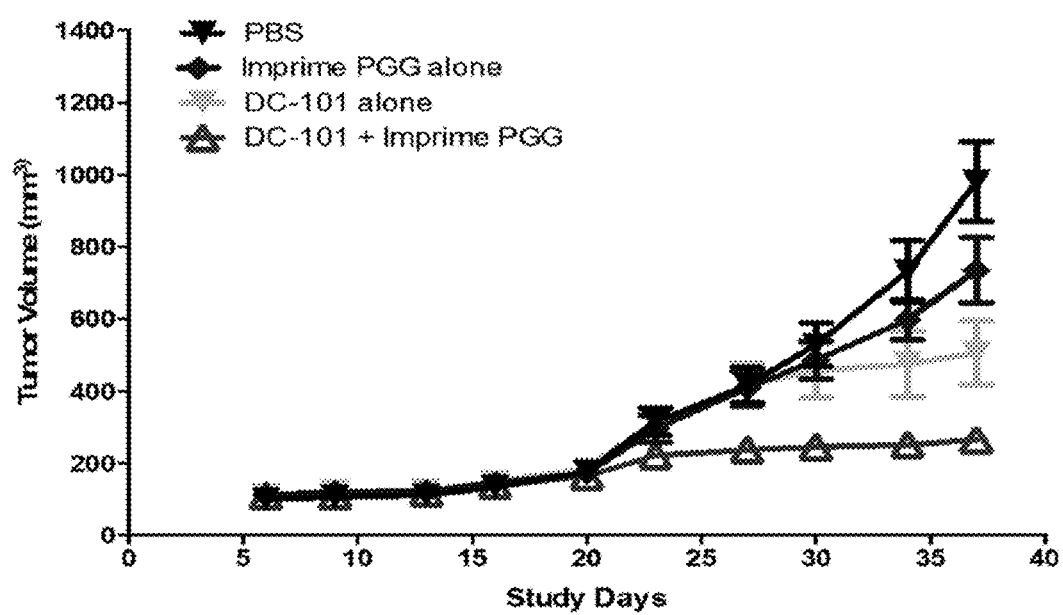
FIG. 16. Results of mouse study using IMPRIME PGG in combination with DC101 antibody.

Treatment groups included vehicle (PBS control), IMPRIME PGG alone, DC101 alone and DC101+IMPRIME PGG. Tumors were randomized to treatment groups once sizes reached a group mean of 150 $mm^3$. The results of the 10 mg/kg treatment groups are shown in FIG. 16.

As is evident from the graph, IMPRIME PGG+DC101 (a complement-activating, non-tumor targeting antibody) acted synergistically to minimize growth of the tumor. Thus, soluble β-glucan in combination with an anti-angiogenic agent (which may or may not be a complement-activating, non-tumor targeting antibody) is an effective cancer therapy.

Example 16

Soluble β-Glucan in Combination with Anti-PD-L1 Antibodies Enhances Tumor-Free Survival:

In another animal study, mice were injected with MC38 tumor cells and randomized into treatment groups. 8 to 12 week-old female C57BL/6 mice were injected with $1 \times 10^6$ MC38 tumor cells, a colon adenocarcinoma that expresses low levels of PD-L1, in a volume of 0.1 ml injected subcutaneously in the flank. Mice were dosed biweekly starting on day 3 with the following agents:
  0.2 ml/mouse vehicle
  1.2 mg/mouse IMPRIME PGG (Biothera, Inc.)
  100 μs/mouse anti-PDL-1 Clone: 10F.9G2 BioXcell Catalog#: BE0101

Blood samples were collected 1 hour prior to dose 1, 2 hours after dose 3, the endpoint and 2 hours after the last dose (day 20). Treatment groups included vehicle (PBS control), IMPRIME PGG alone, anti-PD-L1 antibody alone and anti-PD-L1+IMPRIME PGG. Tumors were randomized to treatment groups once sizes reached a group mean of 150 mm$^3$. The results are shown in Table 10.

TABLE 10

| Treatment Groups | Tumor-free Survivors (day 29) |
| --- | --- |
| Vehicle | 1/18 |
| IMPRIME PGG | 2/18 |
| Anti-PD-L1 | 6/18 |
| Anti-PD-L1 + IMPRIME PGG | 14/17 |

Again, the combination of anti-PD-L1 antibody+soluble β-glucan worked synergistically to effectively enhance tumor-free survival.

It should also be noted that PD-L1 expression on tumors is a biomarker for anti-PD-1 antibody responsiveness. Therefore, because soluble β-glucan induces PD-L1 expression on tumors, soluble β-glucan will also enhance the effectiveness of anti-PD-1 antibodies. This is confirmed by the increased PD-1 expression induced by soluble β-glucan treatment described above.

Example 17

Figure 17A:
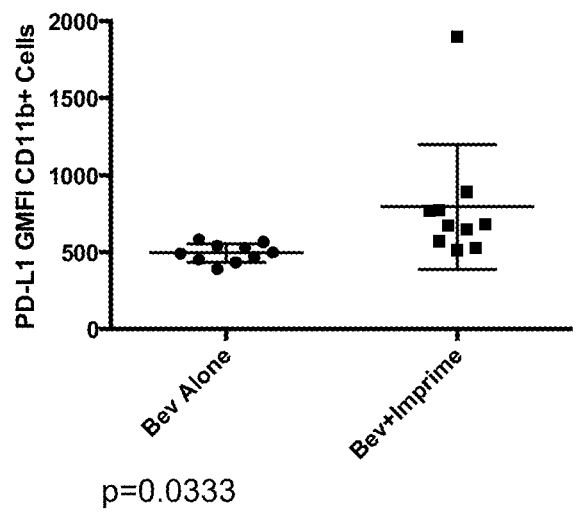
FIG. 17A-17C. In vivo effect on tumor microenvironment of soluble β-glucan and bevicizumab.
Figure 17B:
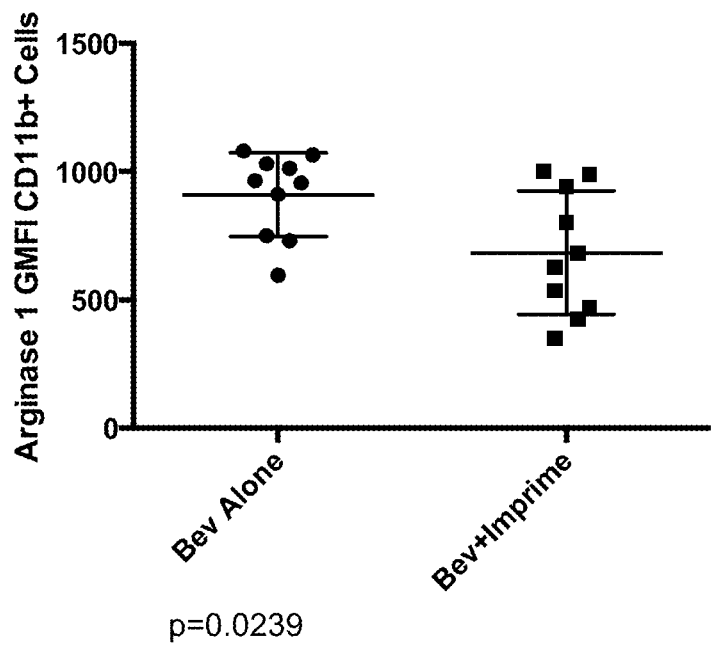
Figure 17C:
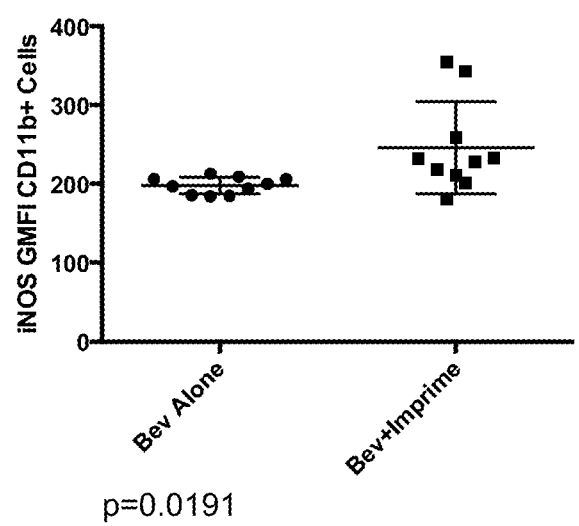

In Vivo Effect on TME of Soluble β-Glucan and Anti-Angiogenic Agents:

Mice bearing H1299 NSCLC tumors were administered bevacizumab (an anti-angiogenic antibody) and IMPRIME PGG as described above for the other mouse studies. As shown in FIG. 17A, the treatment group administered the combination of bevacizumab and IMPRIME PGG showed an increase in PD-L1 expression, FIG. 17B shows down-modulation of Arginase 1 and FIG. 17C shows an increase in iNOS expression in the C11b positive innate immune infiltrate of the TME as compared to that of the group administered bevacizumab alone. Increased iNOS and decreased Arginase 1 are markers indicating an M1, immunostimulatory environment. This data clearly illustrates that soluble β-glucan increases the effectiveness of anti-angiogenic agents and modulates the TME in vivo.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating a subject having cancer, the method comprising administering soluble β(1,6)-[poly-(1,3)-D-glucopyranosyl]-poly-β(1,3)-D-glucopyranose and an anti-PD-L1 antibody, wherein the anti-PD-L1 antibody is a non-complement-activating antibody.

2. The method according to claim 1, wherein the cancer is melanoma, renal cell carcinoma, or lung cancer.

3. The method according to claim 1, wherein the cancer is breast cancer, pancreatic cancer, colon cancer, or B cell lymphoma.

4. The method according to claim 1, wherein the β(1,6)-[poly-(1,3)-D-glucopyranosyl]-poly-β(1,3)-D-glucopyranose and the anti-PD-L1 antibody are in a single formulation.

5. The method according to claim 1, wherein the β(1,6)-[poly-(1,3)-D-glucopyranosyl]-poly-β(1,3)-D-glucopyranose and the anti-PD-L1 antibody are in separate formulations.

6. The method according to claim 1, wherein the β(1,6)-[poly-(1,3)-D-glucopyranosyl]-poly-β(1,3)-D-glucopyranose is derived from yeast.

7. The method according to claim 6, wherein the yeast is *Saccharomyces cerevisiae*.

8. The method according to claim 1, wherein the β(1,6)-[poly-(1,3)-D-glucopyranosyl]-poly-β(1,3)-D-glucopyranose stimulates the subject's immune system.

9. The method according to claim 1, wherein the anti-PD-L1 antibody is an Fc-engineered IgG$_1$ antibody.

10. The method according to claim 1, wherein the anti-PD-L1 antibody is an IgG$_4$ antibody.

11. The method according to claim 1, wherein the β(1,6)-[poly-(1,3)-D-glucopyranosyl]-poly-β(1,3)-D-glucopyranose and the anti-PD-L1 antibody are administered intravenously.

12. The method according to claim 1, wherein the method further comprises administration of a tumor targeting antibody.

13. The method according to claim 1, wherein the method further comprises beta-glucan antibodies.

14. The method according to claim 1, wherein the subject has high response toward soluble β(1,6)-[poly-(1,3)-D-glucopyranosyl]-poly-β(1,3)-D-glucopyranose.

15. A method of stimulating a subject's immune system against cancer cells, the method comprising administering soluble β(1,6)-[poly-(1,3)-D-glucopyranosyl]-poly-β(1,3)-D-glucopyranose and an anti-PD-L1 antibody, wherein the anti-PD-L1 antibody is a non-complement-activating antibody.

16. The method according to claim 15, wherein the immune stimulation comprises activation of M1 macrophages, N1 neutrophils, NK cells, T cells, B cells or dendritic cells.

17. The method according to claim 15, wherein the immune stimulation comprises activation of interleukin-12, interferon-γ, tumor-necrosis factor α, or a combination thereof.

18. A method of removing immune suppression in a tumor microenvironment, the method comprising administering soluble β(1,6)-[poly-(1,3)-D-glucopyranosyl]-poly-β(1,3)-D-glucopyranose and an anti-PD-L1 antibody, wherein the anti-PD-L1 antibody is a non-complement-activating antibody.

19. The method according to claim 18, wherein the method comprises suppression of M2 macrophages, N2 neutrophils, myeloid-derived suppressor cells, or a combination thereof.

* * * * *